United States Patent
Bastiaens et al.

(10) Patent No.: US 11,213,709 B2
(45) Date of Patent: Jan. 4, 2022

(54) BACTERIAL STRAINS AND CONSORTIUM COMPRISING SAME FOR DEGRADING MTBE, TBA AND/OR HCHO

(71) Applicant: VITO NV, Mol (BE)

(72) Inventors: Leen Bastiaens, Mol (BE); Queenie Simons, Mol (BE); Linde Debor, Leipzig (DE); David Moreels, Overijse (BE)

(73) Assignee: VITO NV, Mol (BE)

( * ) Notice: Subject to any disclaimer, the term of this patent is extended or adjusted under 35 U.S.C. 154(b) by 0 days.

(21) Appl. No.: 16/464,962

(22) PCT Filed: Nov. 29, 2017

(86) PCT No.: PCT/EP2017/080885
§ 371 (c)(1),
(2) Date: May 29, 2019

(87) PCT Pub. No.: WO2018/100011
PCT Pub. Date: Jun. 7, 2018

(65) Prior Publication Data
US 2019/0314662 A1    Oct. 17, 2019

(30) Foreign Application Priority Data

Nov. 29, 2016 (EP) .................................. 16201076

(51) Int. Cl.
| | | |
|---|---|---|
| *A62D 3/02* | (2007.01) | |
| *C12N 1/20* | (2006.01) | |
| *B09C 1/10* | (2006.01) | |
| *B09C 1/00* | (2006.01) | |
| *C12R 1/32* | (2006.01) | |

(52) U.S. Cl.
CPC ................ *A62D 3/02* (2013.01); *B09C 1/002* (2013.01); *B09C 1/10* (2013.01); *C12N 1/20* (2013.01); *C12N 1/205* (2021.05); *C12R 2001/32* (2021.05)

(58) Field of Classification Search
CPC .. A62D 3/02; B09C 1/002; B09C 1/10; B09C 2101/00; C12N 1/20; C12R 1/32; C12R 1/01; C02F 3/344
See application file for complete search history.

(56) References Cited

U.S. PATENT DOCUMENTS

2003/0073225 A1    4/2003   Fayolle et al.

OTHER PUBLICATIONS

Cappuyn, A. M. et al. 2010. Quantification of MTBE and TBA Degradation. 11th International Symposium on Computer Applications in Biotechnology. Belgium, Germany. (Year: 2010).*
Cappuyns, A. M. 2010. Quantification of MTBE and TBA biodegradation. 11th International Symposium on Computer Applications in Biotechnology. Leuven, Belgium. (Year: 2010).*

(Continued)

*Primary Examiner* — David W Berke-Schlessel
(74) *Attorney, Agent, or Firm* — Fitch, Even, Tabin & Flannery LLP

(57) ABSTRACT

The present invention provides tools and methods for degrading MTBE, TBA and/or HCHO using abacierial consortium comprising one or more strains selected from *Methylibium* LD3, *Hydrogenophaga* LD1 and/or *Mycobacterium* LD6.

6 Claims, 15 Drawing Sheets

Specification includes a Sequence Listing.

(56) References Cited

OTHER PUBLICATIONS

Leen Bastiaens et al. "MTBE/TBA-degrading bacterial M-consortium as beating heart for Inoculated bioreactor technology." Proceedings of the 2nd European Symposium, Nov. 20-21, 2013, pp. 70-75 (Year: 2013).*

Chistoserdova, Ludmila; et al; "Genome of Methylobacillus flagellatus, Molecular Basis for Obligate Methylotrophy, and Polyphyletic Origin of Methylotroph" Journal of Bacteriology, 189, 4020-4027, 2007 (Year: 2007).*

Liu Haizhou et al. "Biodegradation of Methyl tert-Butyl Ether by Enriched Bacterial Culture," Curr Microbiol (2009) 59: 30-34.

G.M. Zaitsev et al. "Biodegradation of methyl tert-butyl ether by cold-adapted mixed and pure bacterial cultures," Appl Microbiol Biotechnol (2007) 74:1092-1102.

Krassimira Hristova et al. "Naturally Occurring Bacteria Similar to the Methyl tert-Butyl Ether (MTBE)-Degrading Strain PM1 are Present in MTBE-Contaminated Groundwater," Applied and Environmental Microbiology (2003), vol. 69, No. 6, pp. 2616-2623.

Cindy H. Nakatsu et al. "Methylibium petroleiphilum gen. nov., sp. nov., a novel methyl tert-butyl ether-degrading methylotroph of the Betaproteobacteria," International Journal of Systemic and Evolutionary Microbiology (2006), vol. 56, pp. 983-989.

Written Opinion of the International Searching Authority, dated Jan. 25, 2018 for International Application No. PCT/EP2017/080885 (8 pgs).

International Search Report, dated Jan. 25, 2018 for International Application No. PCT/EP2017/080885 (5 pgs).

Wolfgang Ludwig et al. "ARB: a software environment for sequence data," Nucleic Acids Research, 2004, vol. 32, No. 4, pp. 1363-1371.

Stephen F. Altschul et al. "Basic Local Alignment Search Tool," J. Mol. Biol. (1990) 215, pp. 403-410.

David Moreels et al. "Evaluation of the intrinsic methyl tert-butyl ether (MTBE) biodegradation potential of hydrocarbon contaminated subsurface soils in batch microcosm systems," FEMS Microbiology Ecology 49 (2004), pp. 121-128.

Leen Bastiaens et al. "MTBE/TBA-degrading bacterial M-consortium as beating heart for Inoculated bioreactor technology." Proceedings of the 2nd European Symposium, Nov. 20-21, 2013, pp. 70-75.

Linde Debor. Abstract of "Monitoring and optimization of an inoculated bioreactor for remediation of groundwater contaminated with MTBE/TBA." Katholieke Universiteit Leuven, Nov. 2010, 20 pages.

* cited by examiner

*Methylibium sp.* LD3 (Kol_h13)
TGAATTGTAATACGACTCACTATAGGGCGAATTGGGCCCTCTAGATGCATGCT
CGAGCGGCCGCCAGTGTGATGGATATCTGCAGAATTCGCCCTTAGAGTTTGA
TCCTGGCTCAGATTGAACGCTGGCGGCATGCCTTACACATGCAAGTCGAACG
GCAGCACGGGAGCAATCCTGGTGGCGAGTGGCGAACGGGTGAGTAATACAT
CGGAACGTGCCCAGTTGTGGGGGATAGCCCGGCGAAAGCCGGATTAATACCG
CATACGACCTACGGGTGAAAGCGGGGATCGCAAGACCTCGCGCTATTGGAG
CGGCCGATGTCGGATTAGCTAGTTGGTGGGGTAAAAGCCTACCAAGGCTACG
ATCCGTAGCTGGTCTGAGAGGACGACCAGCCACACTGGGACTGAGACACGGC
CCAGACTCCTACGGGAGGCAGCAGTGGGGAATTTTGGACAATGGGCGCAAGC
CTGATCCAGCCATGCCGCGTGCGGGAAGAAGGCCTTCGGGTTGTAAACCGCT
TTTGTCAGGGAAGAAACGGTTTGGGCTAATACCCCGAACTAATGACGGTACC
TGAAGAATAAGCACCGGCTAACTACGTGCCAGCAGCCGCGGTAATACGTAGG
GTGCAAGCGTTAATCGGAATTACTGGGCGTAAAGCGTGCGCAGGCGGCTTTG
CAAGACAGATGTGAAATCCCCGGGCTCAACCTGGGAACTGCATTTGTGACTG
CAAGGCTGGAGTGCGGCAGAGGGGGATGGAATTCCGCGTGTAGCAGTGAAA
TGCGTAGATATGCGGAGGAACACCGATGGCGAAGGCAATCCCCTGGGCCTGC
ACTGACGCTCATGCACGAAAGCGTGGGGAGCAAACAGGATTAGATACCCTGG
TAGTCCACGCCCTAAACGATGTCAACTGGTTGTTGGACGGCTTGCTGTTCAGT
AACGAAGCTAACGCGTGAAGTTGACCGCCTGGGGAGTACGGCCGCAAGGTTG
AAACTCAAAGGAATTGACGGGGACCCGCACAAGCGGTGGATGATGTGGTTTA
ATTCGATGCAACGCGAAAAACCTTACCTACCCTTGACATGTCTAGAAGTTACC
AGAGATGGTTTCGTGCTCGAAAGAGAACTAGAACACAGGTGCTGCATGGCCG
TCGTCAGCTCGTGTCGTGAGATGTTGGGTTAAGTCCCGCAACGAGCGCAACC
CTTGTCATTAGTTGCTACGTAAGGGCACTCTAATGAGACTGCCGGTGACAAA
CCGGAGGAAGGTGGGGATGACGTCAGGTCATCATGGCCCTTATGGGTAGGGC
TACACACGTCATACAATGGCCGGTACAGAGGGCTGCCAACCCGCGAGGGGG
AGCCAATCCCAGAAAACCGGTCGTAGTCCGGATCGCAGTCTGCAACTCGACT
GCGTGAAGTCGGAATCGCTAGTAATCGCGGATCAGCTTGCCGCGGTGAATAC
GTTCCTGGGTCTTGTACACACCGCCCGTCACACCATGGGAGCGGGTTCTGCCA
GAAGTAGTTAGCCTAACCGCAAGGAGGGCGATTACCACGGCAGGGTTCGTGA
CTGGGGTGAAGTCGTAACAAGGTAACCAAGGGCGAATTCCAGCACACTGGCG
GCCGTTACTAGTGGATCCGAGCTCGGTACCAAGCTTGGCGTAATCATG
(SEQ ID NO: 1)

FIGURE 3

*Hydrogenophaga sp.* LD1 (kol_Hyd)
CATGATTACGCCAAGCTTGGTACCGAGCTCGGATCCACTAGTAACGGCCGCC
AGTGTGCTGGAATTCGCCCTTAGAGTTTGATCCTGGCTCAGATTGAACGCTGG
CGGCATGCTTTACACATGCAAGTCGAACGGTAACAGGCCGCAAGGTGCTGAC
GAGTGGCGAACGGGTGAGTAATGCATCGGAACGTGCCCAGTCGTGGGGGAT
AACGCAGCGAAAGCTGTGCTAATACCGCATACGATCTATGGATGAAAGCGGG
GGACCGTAAGGCCTCGCGCGATTGGAGCGGCCGATGTCAGATTAGCTAGTTG
GTGGGGTAAAGGCCCACCAAGGCGACGATCTGTAGCTGGTCTGAGAGGACG
ACCAGCCACACTGGGACTGAGACACGGCCCAGACTCCTACGGGAGGCAGCA
GTGGGGAATTTTGGACAATGGGCGCAAGCCTGATCCAGCAATGCCGCGTGCA
GGAAGAAGGCCTTCGGGTTGTAAACTGCTTTTGTACGGAACGAAAC
GGTCTGGGTTAATACCTCGGGCTAATGACGGTACCGTAAGAATAAGCACCGG
CTAACTACGTGC
CAGCAGCCGCGGTAATACGTAGGGTGCAAGCGTTAATCGGAATTACTGGGCG
TAAAGCGTGCGCAGGCGGTGATGTAAGACAGTCGTGAAATCCCCGGGCTCAA
CCTGGGAATTGCGATTGTGACTGCATCGCTGGAGTGCGGCAGAGGGGGATGG
AATTCCGCGTGTAGCAGTGAAATGCGTAGATATGCGGAGGAACACCGATGGC
GAAGGCAATCCCCTGGGCCTGCACTGACGCTCATGCACGAAAGCGTGGGGAG
CAAACAGGATTAGATACCCTGGTAGTCCACGCCCTAAACGATGTCAACTGGT
TGTTGGGTCTCTTCTGACTCAGTAACGAAGCTAACGCGTGAAGTTGACCGCCT
GGGGAGTACGGCCGCAAGGTTGAAACTCAAAGGAATTGACGGGGACCCGCA
CAAGCGGTGGATGATGTGGTTTAATTCGATGCAACGCGAAAAACCTTACCCA
CCTTTGACATGTACGGAATTTGCCAGAGATGGCTTAGTGCTCGAAAGAGAAC
CGTAACACAGGTGCTGCATGGCTGTCGTCAGCTCGTGTCGTGAGATGTTGGGT
TAAGTCCCGCAACGAGCGCAACCCTTGTCATTAGTTGCTACATTCAGTTGGGC
ACTCTAATGAGACTGCCGGTGACAAACCGGAGGAAGGTGGGGATGACGTCA
AGTCCTCATGGCCCTTATAGGTGGGGCTACACACGTCATACAATGGCCGGTA
CAAAGGGTCGCAAACCCGCGAGGGGGAGCCAATCCATCAAAGCCGGTCGTA
GTCCGGATCGCAGTCTGCAACTCGACTGCGTGAAGTCGGAATCGCTAGTAAT
CGTGGATCAGCATGTCACGGTGAATACGTTCCCGGGTCTTGTACACACCGCC
CGTCACACCATGGGAGCGGGTCTCGCCAGAAGTAGTTAGCCTAACCGCAAGG
AGGGCGATTACCACGGCGGGGTTCGTGACTGGGGTGAAGTCGTAACAAGGTA
GCCGTAAGGGCGAATTCTGCAGATATCCATCACACTGGCGGCCGCTCGAGCA
TGCATCTAGAGGGCCCAATTCGCCCTATAGTGAGTCGTATTACAATTCA
(SEQ ID NO: 2)

FIGURE 4

*Mycobacterium sp.* LD6 (kol_kwit)
TGAATTGTAATACGACTCACTATAGGGCGAATTGGGCCCTCTAGATGCATGCT
CGAGCGGCCGCCAGTGTGATGGATATCTGCAGAATTCGCCCTTAGAGTTTGA
TCCTGGCTCAGGACGAACGCTGGCGGCGTGCTTAACACATGCAAGTCGAACG
GAAAGGCCCTTCGGGGTGCTCGAGTGGCGAACGGGTGAGTAACACGTGGGTG
ATCTGCCCTGCACTTTGGGATAAGCCTGGGAAACTGGGTCTAATACCGAATA
GGACTCCGGACTGCATGGTCTGGGGTGGAAAGCTTTTGCGGTGTGGGATGGG
CCCGCGGCCTATCAGCTTGTTGGTGGGGTGATGGCCTACCAAGGCGACGACG
GGTAGCCGGCCTGAGAGGGTGACCGGCCACACTGGGACTGAGATACGGCCC
AGACTCCTACGGGAGGCAGCAGTGGGGAATATTGCACAATGGGCGCAAGCCT
GATGCAGCGACGCCGCGTGAGGGATGACGGCCTTCGGGTTGTAAACCTCTTT
CAGCACAGACGAAGCGCAAGTGACGGTATGTGCAGAAGAAGGACCGGCCAA
CTACGTGCCAGCAGCCGCGGTAATACGTAGGGTCCGAGCGTTGTCCGGAATT
ACTGGGCGTAAAGAGCTCGTAGGTGGTTTGTCGCGTTGTTCGTGAAAACTCA
CAGCTTAACTGTGGGCGTGCGGGCGATACGGGCAGACTGGAGTACTGCAGGG
GAGACTGGAATTCCTGGTGTAGCGGTGGTATGCGCAGATATCAGGAGGAACA
CCGGTGGCGAAGGCGGGTCTCTGGGCAGTAACTGACGCTGAGGAGCGAAAG
CGTGGGGAGCGAACAGGATTAGATACCCTGGTAGTCCACGCCGTAAACGGTG
GGTACTAGGTGTGGGTTTCCTTCCTTGGGATCCGTGCCGTAGCTAACGCATTA
AGTACCCCGCCTGGGGAGTACGGCCGCAAGGCTAAAACTCAAAGGAATTGAC
GGGGGCCCGCACAAGCGGCGGAGCATGTGGATTAATTCGATGCAACGCGAA
GAACCTTACCTGGGTTTGACATGCACAGGACGCCGGCAGAGATGTCGGTTCC
CTTGTGGCCTGTGTGCAGGTGGTGCATGGCTGTCGTCAGCTCGTGTCGTGAGA
TGTTGGGTTAAGTCCCGCAACGAGCGCAACCCTTGTCTCATGTTGCCAGCACG
TTATGGTGGGGACTCGTGAGAGACTGCCGGGGTCAACTCGGAGGAAGGTGGG
GATGACGTCAAGTCATCATGCCCCTTATGTCCAGGGCTTCACACATGCTACAA
TGGCCGGTACAAAGGGCTGCGATGCCGTGAGGTGGAGCGAATCCTTTCAAAG
CCGGTCTCAGTTCGGATCGGGGTCTGCAACTCGACCCCGTGAAGTCGGAGTC
GCTAGTAATCGCAGATCAGCAACGCTGCGGTGAATACGTTCCCGGGCCTTGT
ACACACCGCCCGTCACGTCATGAAAGTCGGTAACACCCGAAGCCGGTGGCCT
AACCCCTTGTGGGAGGGAGCCGTCGAAGGTGGGATCGGCGATTGGGACGAA
GTCGTAACAAGGTAGCCGTAAGGGCGAATTCCAGCACACTGGCGGCCGTTAC
TAGTGGATCCGAGCTCGGTACCAAGCTTGGCGTAATCATG
(SEQ ID NO:3)

FIGURE 5

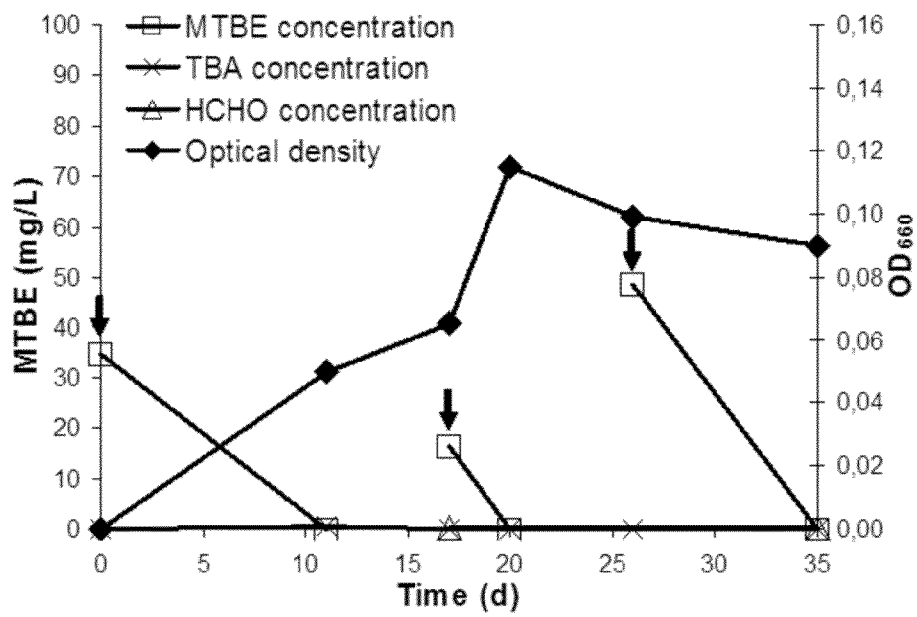
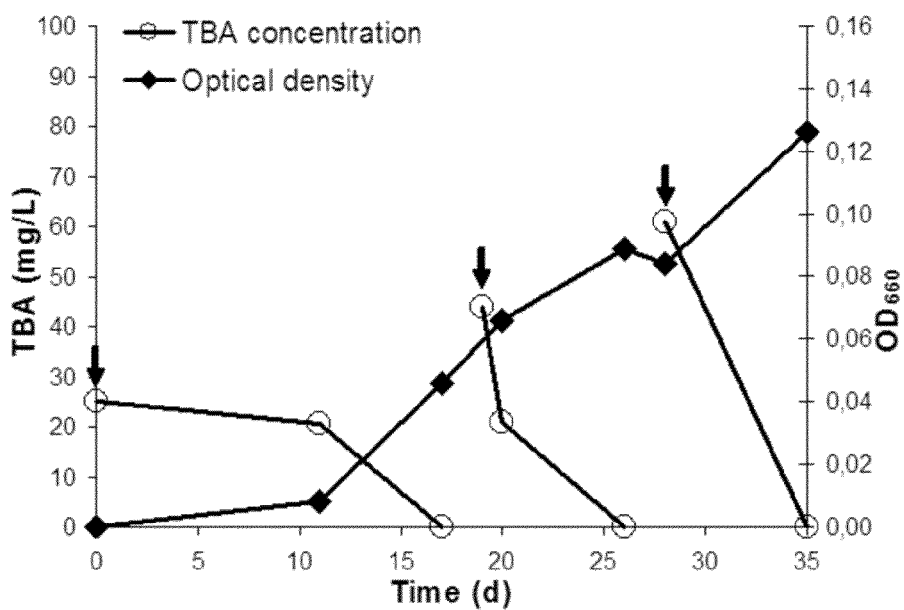
FIGURE 6

(c) *Hydrogenophaga sp.* LD1 (TBA)
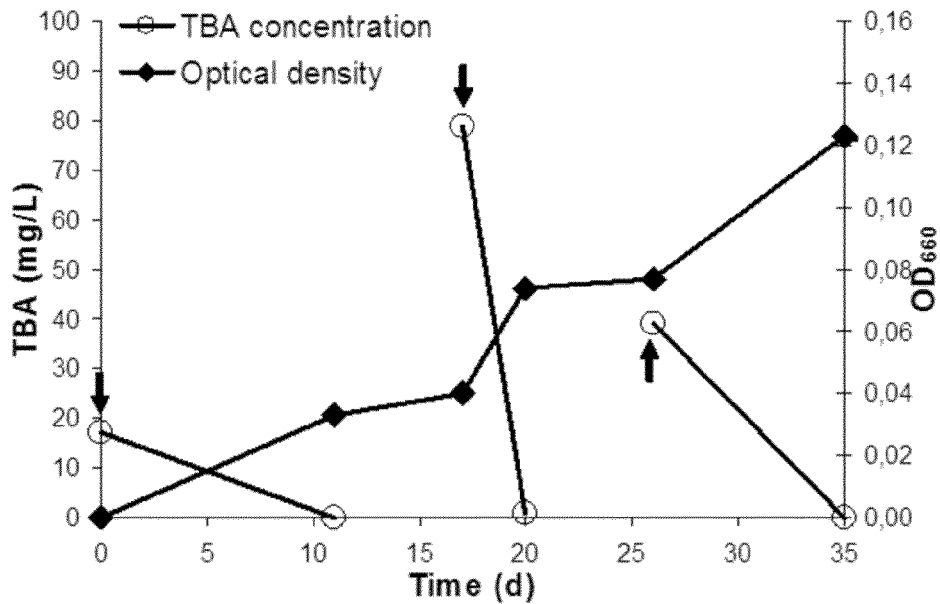
(d) *Mycobacterium sp.* LD6 (HCHO)
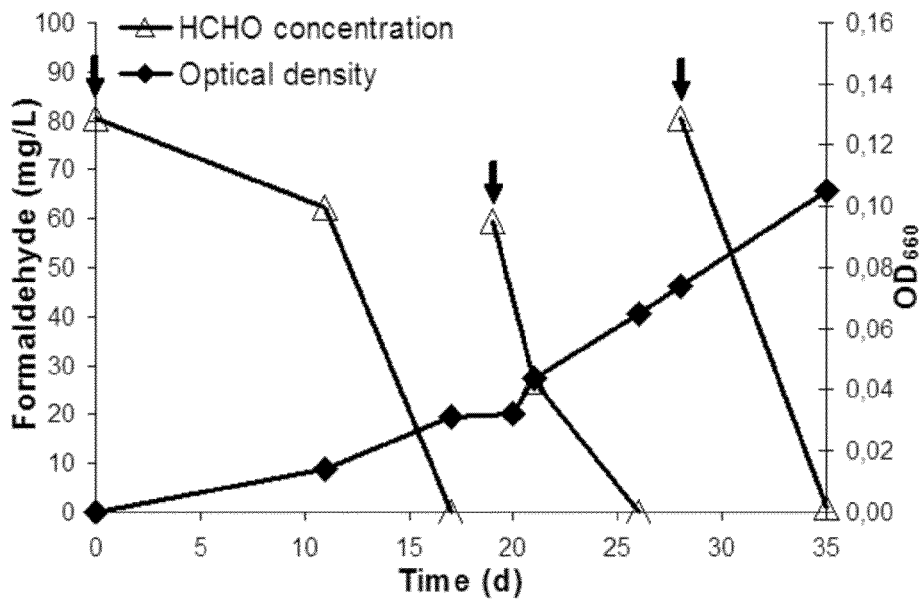
FIGURE 6 (continued)

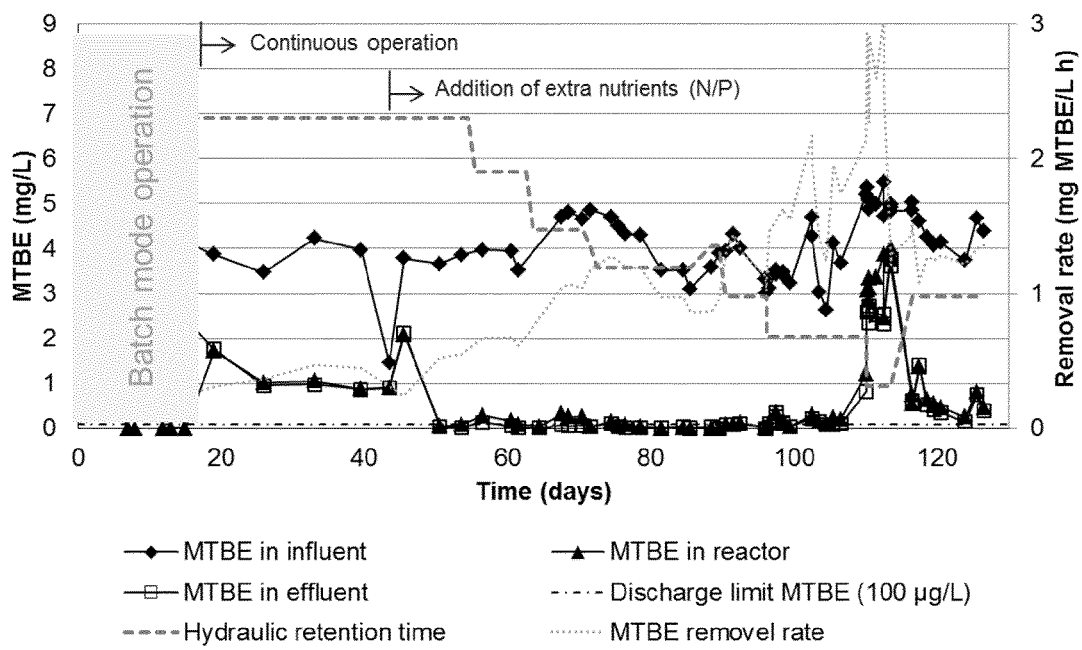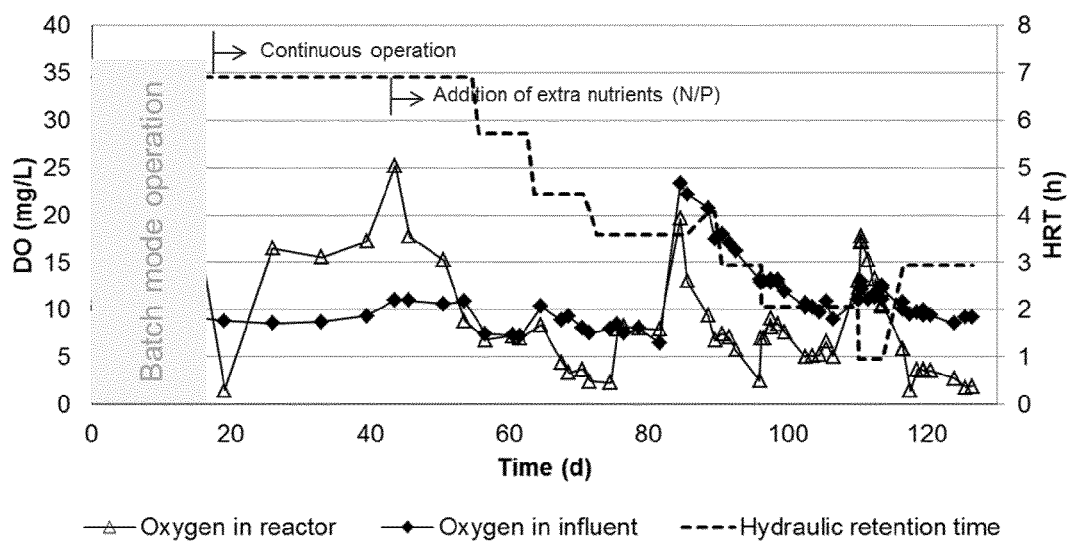
FIGURE 11

BACTERIAL STRAINS AND CONSORTIUM COMPRISING SAME FOR DEGRADING MTBE, TBA AND/OR HCHO

TECHNICAL FIELD

The present invention relates to a bacterial consortium for use in the degradation of methyl-tertiary-butyl-ether (MTBE), tert-butanyl alcohol (TBA) and/or formaldehyde (HCHO) and their applications.

BACKGROUND

Methyl-tertiary-butyl-ether (MTBE) contaminated groundwater is a persistent and worldwide environmental problem. MTBE is a synthetic car fuel additive and is primarily used as a replacement of tetra-ethyl lead to increase the octane rating in lead-free gasoline. An additional advantage of the use of MTBE in gasoline is the improvement of the exhaust fume quality of cars that drive on oxygenated gasoline. However, the presence of MTBE in gasoline results in groundwater contamination with MTBE, mainly due to leaking underground petrol storage tanks. As MTBE has a high solubility in groundwater, MTBE concentrations in groundwater can be relatively high. Tert-butyl alcohol (TBA), also referred to as tert-butanol or tertiary-butyl alcohol, an intermediate in MTBE degradation, and BTEX compounds (benzene, toluene, ethylbenzene and xylenes) are often found in association with MTBE contamination. The presence of MTBE in groundwater poses a threat for drinking water supplies due to the high mobility of MTBE in the earth's subsurface, its recalcitrance and the low taste and odor threshold of MTBE in water. A lot of contamination plumes with MTBE levels exceeding national threshold concentrations show the need for an efficient remediation technology. To treat MTBE contaminated groundwater, bioremediation is regarded as a valuable alternative to physical methods, which are inefficient for treating MTBE and TBA contamination.

To date, a limited number of pure or axenic cultures and mixed cultures with the ability to use MTBE and/or TBA as the only carbon and energy source are known. For most of the mixed cultures, although efforts have been made, the composition is not known and the bacteria responsible for MTBE and/or TBA degradation have not been identified. The biological degradation of MTBE, like the degradation of many other contaminants, is challenged by several difficulties. Most pure cultures grow only very slowly on MTBE, some bacteria readily lose the ability to degrade MTBE and some strains require the addition of specific growth additives.

Moreels et al. (2004; FEMS Microbiology Ecology 49(1): 121-128) compared the capacity of samples from contaminated and non-contaminated soils and aquifers to biodegrade MTBE. Bastiaans et al. (2013; Proc. Aquarehab, Sec. Eur. Symp. P.70-75) and Debor et al. (2010, dissertation KULeuven) refer to a bacterial M-consortium which is allegedly suitable for use in biodegradation of contaminants of ground water. The M-consortium is however not disclosed in an enabling way and cannot be reproduced based on this teaching.

SUMMARY OF THE INVENTION

The present invention provides consortia comprising axenic MTBE, TBA and/or HCHO-degrading cultures, methods for using them and tools for identifying them.

The consortia described herein have a superior capacity to degrade MTBE, TBA and/or HCHO and have been used successfully for MTBE decontamination. More particularly the consortia of the present invention are able to degrade MTBE present in low or high concentrations, as limitation or excess of MTBE does not limit the capacity of the consortia to grow and degrade MTBE, TBA and/or HCHO. The consortia described herein have a relatively high MTBE and TBA degradation rate even at low nutrient concentrations and can be applied in a wide range of boundary conditions (such as low temperature). Furthermore, when using the consortia of the present invention, the biological degradation is complete without accumulation of intermediates.

In contrast to previously described consortia, the consortia of the present invention are very stable and retains their MTBE degradation capacity even when sub-cultivated for several years or when transferred to a different environmental condition.

In a first aspect, the application provides isolated bacterial consortia comprising *Methylibium* strain LD3, which is a methyl-tertiary-butyl-ether (MTBE) degrading strain. Bacterial strain *Methylibium* LD3 has been deposited as LMG P-27480, and is characterized by the presence of a 16S rRNA sequence SEQ ID NO:1. It has been found that the consortia comprising *Methylibium* strain LD3 are highly effective in degrading MTBE and its breakdown products TBA, HIBA and formaldehyde.

It has further been found that consortia comprising *Methylibium* strain LD3 in combination with specific other strains, have a further improved MTBE degrading efficiency. Thus, in particular embodiments, the consortia described herein further comprise *Hydrogenophaga* strain *Hydrogenophaga* LD1 and/or *Mycobacterium* strain *Mycobacterium* LD6. *Hydrogenophaga* strain *Hydrogenophaga* LD1 has been deposited as LMG P-27479 and is characterized by the presence of a 16S rRNA sequence SEQ ID NO:2. *Mycobacterium* strain *Mycobacterium* LD6 was deposited as LMG P-27498 and is characterized by the presence of a 16S rRNA sequence SEQ ID NO:3. In particular embodiments, the consortia described herein comprise *Methylibium* LD3, *Hydrogenophaga* LD1 and *Mycobacterium* LD6 and correspond to the consortium deposited as LMG P-27478 and LMG 27909 (M-consortium). In further particular embodiments of the consortia of the present invention *Methylibium* LD3, *Hydrogenophaga* LD1 and *Mycobacterium* LD6 are present in a ratio of between 1-60%, 40-99% and 0.005-10%, respectively, more particularly between 1-55%, 45-99% and 0.005-2% respectively. In particular embodiments of the consortia of the present invention *Methylibium* LD3, *Hydrogenophaga* LD1 and *Mycobacterium* LD6 are each present between $10^2$ to $10^8$ cells/ml, such as between $10^4$-$10^8$ copies per ml *Methylibium* LD3, $10^6$-$10^9$ copies per ml *Hydrogenophaga* LD1 and $10^2$-$10^6$ copies per ml *Mycobacterium* LD6, respectively. In particular embodiments of the consortia of the present invention *Methylibium* LD3, *Hydrogenophaga* LD1 and *Mycobacterium* LD6 are present in relative abundances of about (%/%/%) 1-55/45-99/0.005-2, such as in relative abundances of 4.5/95.5/0.03, 51.3/48.7/0.005, 47.6/52.4/0.008, 2.1/97.9/0.006, 7.3/92.6/0.02, 36.3/63.6/0.07, 1.3/98.4/0.3, or 13.9/86/0.02.

In particular embodiments, the relative concentration of *Methylibium* LD3, *Hydrogenophaga* LD1 and/or *Mycobacterium* LD6 as measured on carrier material during and after degradation of MTBE is 0.01-99.98%, 0.01-99.98% and 0.01-34%, respectively, as determined by q-PCR. In particular embodiments, the relative concentration of *Methyli-* bium LD3, *Hydrogenophaga* LD1 and/or *Mycobacterium* LD6 in the consortium as measured on carrier material during and after degradation of MTBE iunder non-sterile conditions with real groundwater is 0.1-86%, 0.1-10%, <0.1-7%, respectively, as determined by q-PCR, and 0.1-57%, <0.1-23% and <0.1-35%, respectively as determined via FISH analyses (Fluorescence in-situ Hybrisidisation) using specific probes.

The bacterial strains and consortia described herein are particularly advantageous for the degradation of methyl-tertiary-butyl-ether (MTBE), tert-butanol (TBA), hydroxy-isobutyric acid (HIBA), formaldehyde (HCHO) and/or BTEX-compounds in an MTBE, TBA, HIBA, HCHO and/or BTEX contaminated medium.

In particular embodiments, the bacterial consortia described herein comprising *Methylibium* LD3, *Hydrogenophaga* LD1 and/or *Mycobacterium* LD6 strain, have a maximal observed MTBE degradation rate of 10-64 mg MTBE per g dry weight biomass per hour and/or a TBA degradation rate of 30-80 mg TBA per g dry weight biomass per hour.

Accordingly, a further aspect provides methods for degrading methyl-tertiary-butyl-ether (MTBE), tert-butanol (TBA), hydroxyisobutyric acid (HIBA) and/or formaldehyde (HCHO) in MTBE, TBA, HIBA and/or HCHO contaminated medium making use of the bacterial strains and/or consortia described herein. In particular embodiments, such methods comprise the steps of: (i) providing a consortium as described herein; and (ii) treating the contaminated medium with said consortium to degrade at least a portion of said contamination. In particular embodiments, the treatment step takes place in a bioreactor or in situ by addition of the consortium to the contaminated medium. The contaminated medium in situ may be at a temperature of about 10° C., in particular between 5° C. and 15° C., in particular between 7° C. and 13° C.

In particular embodiments of the methods of the present invention, the consortium is added to the contaminated medium at a cell count between $10^2$ to $10^8$ cells/ml. In particular embodiments, the methods involve providing a consortium having a relative concentration of *Methylibium* LD3, *Hydrogenophaga* LD1 and/or *Mycobacterium* LD6 as described above. According to particular embodiments of the present invention, the methods comprise determining the concentration of the MTBE, TBA, HIBA and/or HCHO in the medium, and/or comprise determining the degradation rate of the MTBE, TBA, HIBA and/or HCHO in the medium.

In particular embodiments of the present invention, the contaminated medium is selected from the group consisting of contaminated soil, contaminated sludge, contaminated sediment, contaminated dredge tailing, contaminated chemical waste, contaminated fluid and contaminated water.

In a further aspect, the present invention provides methods for detecting the presence of a *Methylibium* LD3, *Hydrogenophaga* LD1 and/or *Mycobacterium* LD6 microorganism in a sample comprising identifying the presence of a sequence corresponding to SEQ ID NO:1 (FIG. 3), SEQ ID NO:2 (FIG. 4) or SEQ ID NO:3 (FIG. 5), respectively in said sample. In particular embodiments, these methods comprise contacting said sample with a primer or probe capable of hybridizing specifically to, or amplifying a sequence specific for, SEQ ID NO:1, SEQ ID NO:2 or SEQ ID NO:3 and determining the presence of a hybridization signal or an amplification product indicative of the presence of *Methylibium* LD3, *Hydrogenophaga* LD1 and/or *Mycobacterium* LD6, respectively in the sample.

In yet a further aspect, the present invention provides isolated bacterial strains which are of particular interest for use in the degradation of MTBE, TBA, HIBA and/or HCHO. More particularly, the invention provides an isolated MTBE, TBA, HIBA and formaldehyde degrading *Methylibium* strain, which is characterized by the presence of 16S RNA sequence SEQ ID NO:1 and/or corresponds to strain *Methylibium* LD3, deposited as LMG P-27480. In a further embodiment, the invention provides an isolated tert-butanol (TBA) degrading *Hydrogenophaga* strain, which is characterized by the presence of 16S RNA sequence SEQ ID NO:2 and/or which corresponds to strain *Hydrogenophaga* LD1 deposited as LMG P-27479. The present invention further provides an isolated formaldehyde (HCHO) degrading *Mycobacterium* strain, which is characterized by the presence of 16S RNA sequence SEQ ID NO:3 and/or which corresponds to strain *Mycobacterium* LD6 deposited as LMG P-27498. Said isolated strains may be used in the degradation of MTBE, TBA, HIBA, formaldehyde and/or HCHO.

In yet a further aspect, the present invention provides isolated nucleic acid sequences which are of interest in the detection of the bacterial strains and consortia described herein. More particularly, the invention provides isolated polynucleotides comprising or consisting of the sequence represented by SEQ ID NO:1, SEQ ID NO:2 or SEQ ID NO:3, which correspond to specific 16SRNA sequences for the bacterial strains described herein.

BRIEF DESCRIPTION OF THE FIGURES

The present invention is illustrated by the following Figures which are to be considered as illustrative only and do not in any way limit the scope of the invention.

FIG. 3 illustrates the sequence of the 16S rRNA of *Methylibium* sp. LD3

FIG. 4 illustrates the sequence of the 16S rRNA of *Hydrogenophaga* sp. LD1

FIG. 5 illustrates the sequence of the 16S rRNA of *Mycobacterium* sp. LD6

FIG. 6 illustrates degradation of MTBE, TBA or HCHO by and corresponding growth of the pure bacterial strains isolated from the M-consortium. The arrows depict the time of the addition of MTBE, TBA or HCHO substrate. Growth was monitored by $OD_{660}$ measurements.

FIG. 11 illustrates implemented HRT, measured MTBE concentrations and calculated MTBE removal rates (a) and dissolved oxygen concentrations (b) in a 7 L bioreactor system containing expanded clay as a carrier material, inoculated with the M-consortium, and fed with a MTBE containing groundwater. Indicated are the batch operation period (grey area), start of the continuous operational phase and the start of the nutrient addition (N/P, 2.5 mg/L $K_2HPO_4.3H_2O$ and $KNO_3$).

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this implies that embodiments are also envisaged which consist essentially of the recited elements or steps.

The recitation of numerical ranges by endpoints includes all numbers and fractions subsumed within the respective ranges, as well as the recited endpoints.

The term 'isolated' refers to material that is substantially or essentially free from compounds that normally accompany it as found in its native state. For instance, the term 'isolated' may refer to fact that the consortium is 'isolated', 'separated' or 'purified' from the medium or sample comprising MTBE, TBA, HIBA and/or HCHO. Alternatively, this term may also refer to the fact that the consortium is isolated from microorganisms other than these present in the consortium of the present invention but normally present in its natural environment.

A 'bacterial consortium' is an association of two or more bacterial species with the objective of participating in a common activity for achieving a common goal. The term 'MTBE' refers to methyl-tertiary-butyl-ether and to methyl-tertiary-butyl-ether-like compounds. The term 'TBA' refers to tert-butany alcoholl. The term 'HCHO' refers to formaldehyde. The term 'HIBA' refers to hydroxyisobutyric acid. The term BTEX refers to the mono-aromatics benzene, toluene, xylenes and ethylbenzene.

In a first aspect, the present invention provides isolated bacterial consortia which are methyl-tertiary-butyl-ether (MTBE) degrading consortia. Indeed, bacterial strains have been identified which are of particular interest when used in a bacterial consortium for the degradation of MTBE, TBA, HIBA, and/or HCHO.

Figure 2:
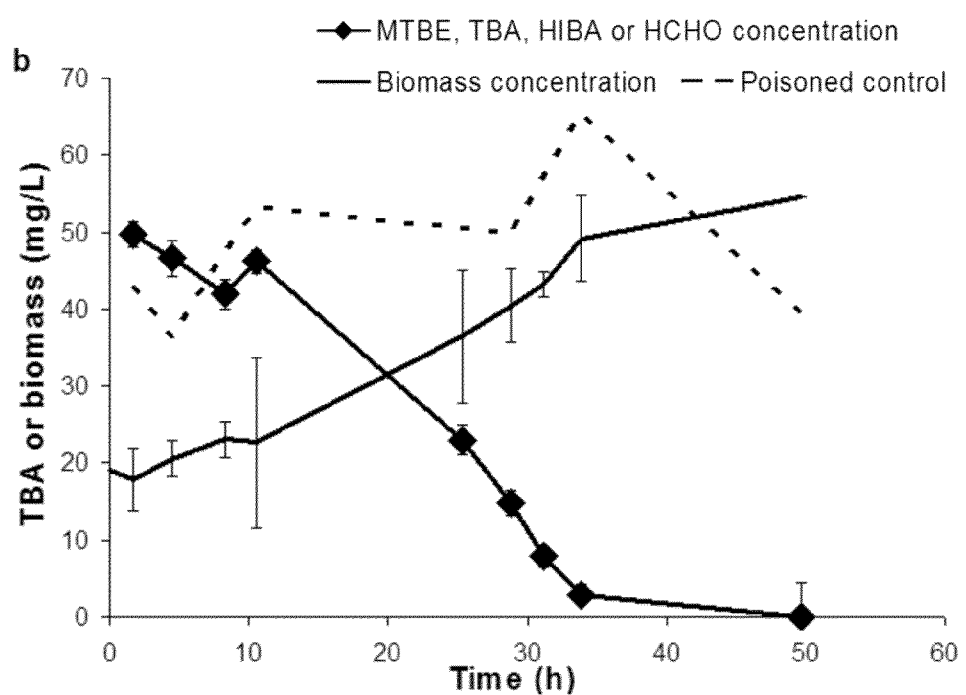
FIG. 2 illustrates the stability of the M-consortium to degrade MTBE over a long time period in labscale conditions in a minimal mineral medium with several re-additions of MTBE as sole carbon source.
Figure 2:
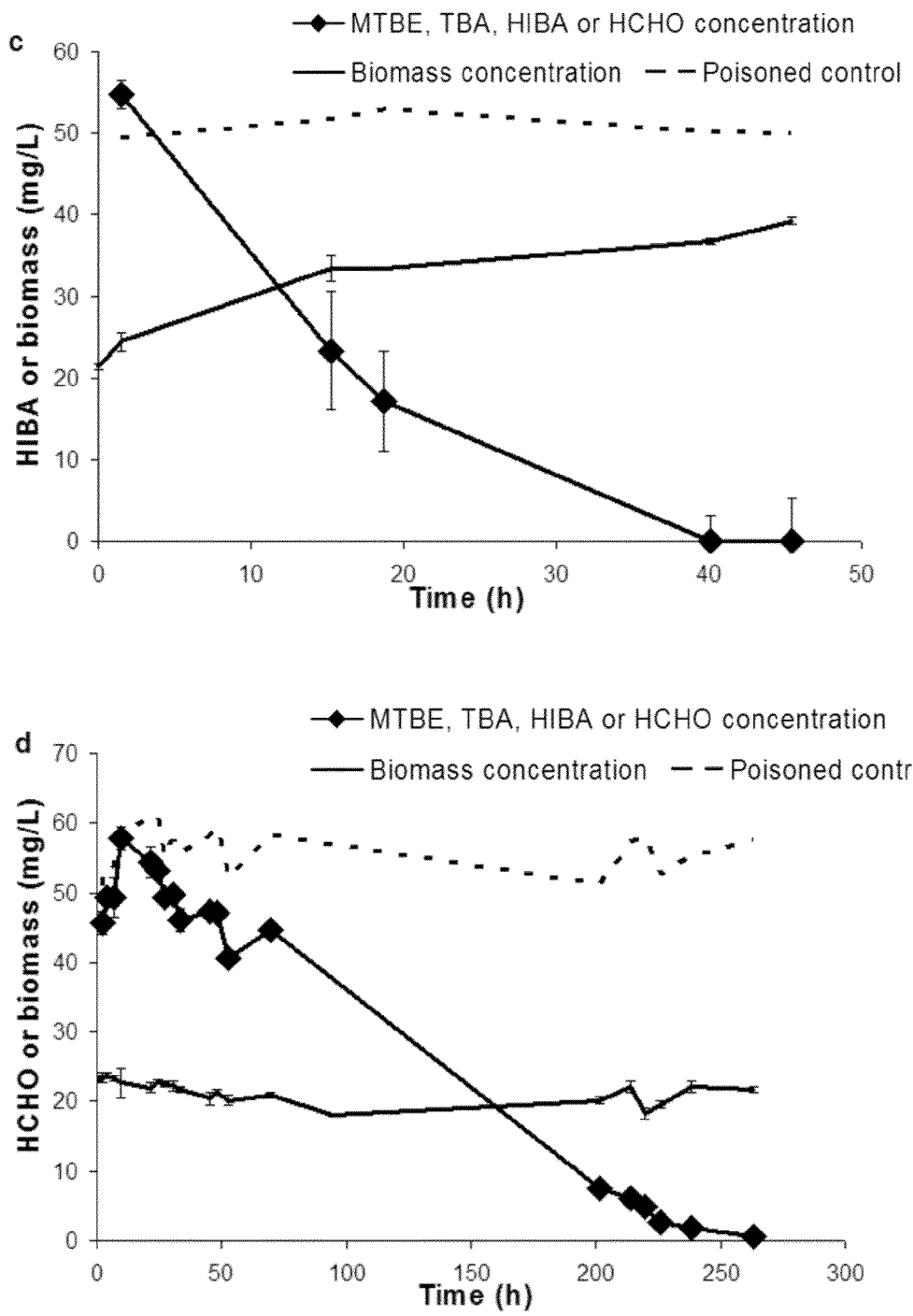

More particularly it has been found that bacterial strain *Methylibium* strain LD3 is capable of efficiently degrading MTBE, TBA, HIBA and formaldehyde. *Methylibium* strain LD3 has been deposited as LMG P-27480, at the Belgian co-ordinated collections of Micro-organisms, at Laboratorium voor Microbiologie, Universiteit Gent (UGent) K.L. Ledeganckstraat 35B-9000 Gent by Dirk Fransaer (in his capacity as managing director of VITO NV) on Feb. 28, 2013. Bacterial strain *Methylibium* strain LD3 is further characterized by the presence of a 16S rRNA sequence SEQ ID NO:1 (FIG. 2). It has been found that the consortia comprising *Methylibium* strain LD3 are highly effective in degrading MTBE as described above.

It has further been found that the MTBE degrading capacity of the bacterial consortia of the present invention are further improved by the presence of one or more TBA degrading strains and/or one or more HCHO degrading strains. Accordingly, the isolated bacterial consortia described herein may further comprise, in addition to strain *Methylibium* LD3, a TBA degrading bacterial strain, more particularly a strain from the species *Hydrogenophaga*, most particularly *Hydrogenophaga* strain *Hydrogenophaga* LD1. This latter strain has been deposited as LMG P-27479, at the Belgian co-ordinated collections of Micro-organisms, at Laboratorium voor Microbiologie, Universiteit Gent (UGent) K. L. Ledeganckstraat 35, B-9000 Gent by Dirk Fransaer (in his capacity as managing director of VITO NV) on Feb. 28, 2013. Bacterial strain *Hydrogenophaga* LD1 is further characterized by the presence of a 16S rRNA sequence SEQ ID NO:2 (FIG. 3).

Similarly, the isolated bacterial consortia described herein may further comprise, in addition to *Methylibium* strain LD3, a HCHO degrading bacterial strain, more particularly a strain from the species *Mycobacterium*, most particularly *Mycobacterium* LD6. The strain *Mycobacterium* LD6 has been deposited as LMG P-27480 at the Belgian co-ordinated collections of Micro-organisms, at Laboratorium voor Microbiologie, Universiteit Gent (UGent) K. L. Ledeganckstraat 35, B-9000 Gent by Dirk Fransaer (in his capacity as managing director of VITO NV) on Mar. 29, 2013. Bacterial strain *Mycobacterium* LD6 is further characterized by the presence of a 16S rRNA sequence SEQ ID NO:3 (FIG. 4).

The consortia of the present invention may further comprise organisms other than *Methylibium* LD3; *Hydrogenophaga* LD1 and/or *Mycobacterium* LD6. Indeed, it can be envisaged that in order to further improve efficiency of MTBE degradation and/or in order to achieve complementary degradation of other contamination products, other strains can be present in the consortia of the present invention. This can be for interest, for example, in the treatment of mixed waste streams. Accordingly, in particular embodiments the consortia described herein may comprise organisms having different specificities for given contaminants or their degradation intermediates. For instance, the consortium may comprise Proteobacteria other than the MTBE, TBA, HIBA and/or HCHO degrading *Methylibium* species and/or the TBA degrading *Hydrogenophaga* species of the present invention. Examples thereof include but are not limited to *Thermomonas* species, *Ralstonia* species, *Hyphomycrobium* species, *Pseudomonas* species and *Sphingomas* species.

Additionally or alternatively, the bacterial consortia of the present invention may comprise other strains which have been shown to be useful in the degradation of MTBE, TBA and/or HCHO. Examples thereof include but are not limited to bacteria such as *Methylibium petroleiphilum* PM1, *Methylibium* sp. UC1, *Methylibium* sp.R8, *Mycobacterium austroafricanum* IFP2012, *Mycobacterium austroafricanum* IFP2015, *Mycobacterium* sp. UC3, *Aquincola tertiaricarbonis* L108, *Hydrogenophaga flava* ENV735, *Rhodococcus ruber* 1-1889, *Rhodococcus aetherivorans* 10bc312, *Variovorax paradoxus* CL-8 and strain CIP 1-2052.

Additionally or alternatively, the consortia of the present invention may further comprise growth components, chemical additives, carrier materials and/or preservatives. The M-consortium is regularly cultured in a standard mineral medium (WXP medium) containing MTBE (i.e. 10 mg/ml). Examples of growth components thus include components present in or added to WXP medium, such as carbon sources. A further example of a preservative includes but is not limited to glycerol. Examples of carriers include but are not limited to expanded clay, biochips, coconut shells, glass beads, polysterol granulates, sponges, etc.

As detailed above, the bacterial consortia of the present invention have been found to be particularly effective in the degradation of MTBE and more particularly in the degradation of MTBE, TBA, HIBA and HCHO in contaminated media. The presence of MTBE, TBA, HIBA and HCHO can be measured using techniques known by a skilled person in the art. Methods which may possibly be used are described in the examples disclosed in the present application. Different methods may be used to calculate the specific degradation rate. The degradation rate may be expressed as nmol MTBE/day/cell, however, in the present application mg MTBE/g DW (Dry Weight) h and mg MTBE/L h are preferably used. In particular embodiments, the bacterial consortia of the present invention are capable of degrading MTBE with an MTBE degradation rate of between 10-64 mg MTBE/g DW (Dry Weight) h and/or of degrading TBA with a TBA degradation rate of between 30 and 80 mg TBA/g DW (dry weight) h.

Besides the MTBE degradation rate, the bacterial consortia of the present invention may further be characterized by growth rate, biomass yield and transient TBA accumulation. The kinetics of the degradation is determined by the growth rate and the MTBE degradation rate. In particular embodiments of the present invention, the bacterial consortia degrade MTBE, TBA, HIBA and BTEX at initial concentrations of >120 mg/L MTBE/TBA and 80 mg/L of BTEX and are able to degrade MTBE, TBA and BTEX to concentrations below the detection limits for Gas Chromatography-Mass Spectrometry (GC-MS), i.e., 2 µg/L MTBE, 65 µg/L TBA and 0.5 µg/L BTEX, with associated production of biomass. The calculation of the MTBE degradation rate is also exemplified in the Examples disclosed in the present application.

According to a further aspect, the application provides methods for degrading methyl-tertiary-butyl-ether (MTBE), tert-butyl alcohol (TBA) and/or formaldehyde (HCHO) in MTBE, TBA and/or HCHO contaminated medium.

In particular embodiments, the methods for degrading MTBE, more particularly MTBE, TBA and/or HCHO comprise the step of treating the contaminated medium with the isolated micro-organisms and/or the consortia described herein.

As envisaged herein, the treatment may take place ex situ or in situ. In particular embodiments, the medium is groundwater.

Different practical ways of contacting the contaminated medium with the isolated bacteria and/or consortia described herein are envisaged. For example, biodegradation of MTBE in groundwater can be performed either by pumping and treating the groundwater in a bioreactor inoculated with the micro-organism(s) and/or the consortium, or, by the addition of the micro-organism(s) and/or the consortium to the contaminated medium being the subsurface.

In general, a variety of bioreactors known to those skilled in the art may be used in the methods of the invention. Suspended growth reactors, such as membrane reactors, standard continuously stirred tank reactors and activated sludge systems may be used. Alternatively, fixed film reactors, such as fluidized bed reactors or fixed support reactors, may also be used, if desired. Alternatively, or complementary, the bacteria can be confined in biobarriers, biofilters, and/or biopiles. Such biobarriers, biofilters and biopiles are commonly used by the skilled person in the art to prevent the spreading of a pollution, for example when disposed between the pollution source and groundwater located downstream of said pollution.

To date, only a handful studies describe the development of bioreactors that treat groundwater contaminated with MTBE.

The isolated micro-organism and/or the bacterial consortium of the present invention is used in the methods of the present invention to degrade methyl-tertiary-butyl-ether (MTBE), tert-butyl alcohol (TBA) and/or formaldehyde (HCHO) in an MTBE, TBA and/or HCHO contaminated medium. The term 'degrade' implies that the final concentration of the MTBE, TBA and/or HCHO contamination is reduced compared to the initial concentration. In particular embodiments, after degradation the final concentrations reach or are lower than the regulatory limits set by the official authorities. More preferably, the final concentration of the contaminant(s) is not detectable anymore. Concentrations of MTBE and TBA in groundwater can be relatively high (e.g. up to 830 mg/L MTBE and more and up to more than 78 mg TBA have been reported). However, generally, groundwater concentrations are around 0.5-50 mg/L. Several countries, including Belgium, have adopted regulatory limits for MTBE in groundwater. The intervention level for groundwater has been determined to be 300 µg/L MTBE, in Belgium, 200 µg/L MTBE in Germany and Switzerland and 9.4 mg/L MTBE in the Netherlands. However, the clean-up levels are preferably lower. Thus, according to particular embodiments, the methods described herein involve the degradation of MTBE so as to be reduced to less than 300 µg/L or less, more particularly to 200 µg/L or less, most particularly to less than 100 µg/L. In particular embodiments the methods described herein ensure a clean-up level to 100 µg/L MTBE.

TBA, a stable intermediate of MTBE degradation, is often found in association with MTBE contamination, i.e. at concentrations varying from 4.10-4 to 78 mg/L. In Belgium, a level below of 660 µg/L in groundwater is recommended. BTEX compounds (benzene, toluene, ethylbenzene and xylene) are well known co-contaminants in MTBE-contaminated groundwater. BTEX are present in gasoline at about 18% v/v and were reported to be present in groundwater in Europe at concentrations of 0.2-147 mg/L. Thus in particular embodiments, the methods of the present invention ensure the degradation of TBA to be reduced to less than 700 µg/L.

The inventors found that the micro-organisms and/or consortia of the invention can be applied for biodegradation of MTBE and TBA in a wide range of boundary conditions, including the boundary conditions typical for in situ bioaugmentation (low temperature and low dissolved oxygen concentration) as well as the conditions present bioreactors for ex situ bioremediation (room temperature, neutral pH, high dissolved oxygen concentrations and low nutrient concentrations). The inventors found that, when using a pilot scale bioreactor for pump-and-treat of MTBE-contaminated groundwater with MTBE (5 mg/L MTBE) a minimal hydraulic retention time of 1.6 hours is sufficient for removal of MTBE to below the reinfiltration limit of 100 µg/L MTBE in groundwater. It has been demonstrated that also lower MTBE-concentrations (<1 mg/L) can be efficiently removed till below the discharge limit of 100 µg/L MTBE, where the hydraulic retention time could be reduced till 1 hour. Further, it has been demonstrated that TBA (6 mg/L) could be efficiently removed till below detection limit.

In the methods of the present invention, the density of cells of the isolated micro-organisms and/or consortium used may vary. In particular embodiments, the consortium is added having a cell count between $10^2$ to $10^8$ CFU/ml, more preferably between $10^5$ and $10^7$ CFU/ml. In aquifer matrices the isolated micro-organisms and/or consortium used is preferably $10^6$ CFU/g aquifer, though smaller inocula may also initiate the degradation. In a bioreactor application, it is envisaged that the isolated micro-organisms and/or consortium used is preferably between $10^3$ to $10^8$ CFU/g carrier material.

In particular embodiments, the methods of the present invention for the degradation of MTBE, TBA and/or HCHO are performed by contacting the contaminated medium with a consortium as described herein. More particularly, the consortium comprises *Methylibium* LD3, *Hydrogenophaga* LD1 and *Mycobacterium* LD6. The relative concentration of these strains in the consortium may vary. In particular embodiments, the absolute concentration of *Methylibium* LD3, *Hydrogenophaga* LD1 and/or *Mycobacterium* LD6 in the consortium used to treat the contaminated medium is between $10^4$-$10^8$ copies per ml, $10^6$-$10^9$ copies/ml and $10^2$-$10^6$ copies/ml, respectively. In particular embodiments of the consortia of the present invention *Methylibium* LD3, *Hydrogenophaga* LD1 and *Mycobacterium* LD6 are present between in relative abundances of (%/%/%) 1-60/40-99/0.005-10, more particularly 1-55/45-99/0.005-2, such as in relative abundances of 4.5/95.5/0.03, 51.3/48.7/0.005, 47.6/52.4/0.008, 2.1/97.9/0.006, 7.3/92.6/0.02, 36.3/63.6/0.07, 1.3/98.4/0.3, and 13.9/86/0.02, or in particular embodiments, relative abundances of 18-25%, 72-78% and 1-2%, respectively. According to particular embodiments, the methods for the degradation of MTBE, TBA, HIBA and/or HCHO further comprise determining the degradation of MTBE, TBA, HIBA and/or HCHO. Thus, in particular embodiments of the methods of the present invention an additional step may be introduced wherein the concentration of the MTBE, TBA, HIBA and/or HCHO in the medium and/or the degradation rate of the MTBE, TBA, HIBA and/or HCHO in the medium is determined. Methods for determining the concentration of MTBE, TBA, HIBA and/or HCHO and/or calculating the degradation rate of the MTBE, TBA, HIBA and/or HCHO are described herein above and in the examples of the present application.

The methods provided herein relate to the degradation of MTBE, TBA, HIBA and/or HCHO in a contaminated medium. The term 'medium', as used herein is meant to include, but is not limited to soil, aquifer, sludge, sediment, dredge tailing, chemical waste, and other fluids such as water. 'Soil' is a natural body consisting of layers of primarily mineral constituents of variable thicknesses, which differ from the parent materials in their texture, structure, consistence, color, chemical, biological and other physical characteristics. Soil forms a structure that is filled with pore spaces, and can be thought of as a mixture of solids, water and air (gas). 'Aquifer' refers to the soil material from the saturated zone where groundwater is flowing under the influence of hydraulic gradients. 'Sludge' refers to the residual, semi-solid material left from industrial wastewater, or sewage treatment processes. It can also refer to the settled suspension obtained from conventional drinking water treatment, and numerous other industrial processes. 'Dredge tailing' is the material that is washed or sorted away during dredge activities thereby digging up material (sand, gravel, dirt, etc.). 'Chemical waste' is a waste that is made from harmful chemicals (mostly produced by large factories). In the present context, the waste may refer to fuel waste, waste contaminated with ether derivatives, in particular to MTBE, TBA and/or HCHO. A 'fluid' is a substance that continually deforms (flows) under an applied shear stress. Fluids are a subset of the phases of matter and include liquids, gases, plasmas and, to some extent, plastic solids. According to the present application, the liquid may be water, in particular groundwater or drinking water.

In particular embodiments, the methods of the present invention involve the use of one or more of the isolated bacterial strains described herein. In these embodiments of the methods for degrading MTBE, TBA and/or HCHO in MTBE, TBA and/or HCHO contaminated medium of the present invention, the strains of the present invention may be added simultaneously, partial sequentially or sequentially to the contaminated medium. In this context, the isolated strains may be contacted with the medium in the same physical space (e.g. bioreactor) or may be contacted with the medium in sequentially placed bioreactors.

In particular embodiments, the methods of the present invention are combined with the removal of other contaminants than MTBE, TBA, HIBA and/or HCHO. This may in some embodiments, increase the efficiency of the removal of MTBE, TBA, HIBA and/or CHCO removal ensured by methods described herein. Thus, in particular embodiments, the methods of the invention are combined with the removal of iron from contaminated medium. In particular embodiments the methods of the present invention are used in combination with the removal of iron from groundwater. For iron removal, the medium may be treated in a pre- or post-treatment step using an iron removal unit, preferably comprising an oxidation unit and a sand filter.

Yet a further aspect envisaged herein relates to methods for the identification of the bacterial strains and consortia described herein. These may be used alone or in combination with the methods for the degradation of MTBE, TBA, HIBA and/or HCHO described herein. Indeed, in particular embodiments, it may be of interest to check the bacterial culture for the presence of the bacterial strains and/or consortia of the invention.

In general, bacteria present in a (complex) mixture or composition may be identified using diverse analytic methods or techniques. For instance, methods for said identification may be based on the metabolic capacity of said bacteria (i.e. antibiotic resistance, compound fermentation, . . . ), based on their expression profile (i.e. expression of specific membrane or intracellular proteins, . . . ), and/or based on the presence of specific cellular components (i.e. presence of specific polynucleotide sequences or specific internal proteins, . . . ).

All of these methods may be used alone or combined if necessary. In the present case, independently of the method applied, reference strains may be used. In particular embodiments, the methods for the identification of *Methylibium* LD3, *Hydrogenophaga* LD1 and/or *Mycobacterium* LD6, or a consortium described herein comprising one or more of these strains may involve the use of the strain(s) as deposited as LMG P-27480, LMG P-27479, LMG P-27498 and/or LMG P-27478 or LMG P-27909 as reference strain(s) or consortium. For instance, the bacteria as described herein may be identified using a selection medium containing MTBE, TBA and/or HCHO as only carbon source. Additionally or alternatively, presence of specific membrane proteins can be visualized using specific antibodies. In addition, bacteria can be identified by protein fingerprinting using, for instance, PAGE. Another alternative method may be polynucleotide analysis using hybridization, amplification and/or sequencing techniques. Independently from the method applied, the skilled artisan is able to adapt the detection means to the kind and amount of sample analyzed.

According to the present invention, the bacterial strains used herein may also be identified using 16S rRNA gene PCR-denaturing gradient gel electrophoresis (PCR-DGGE). Additionally or alternatively, fluorescent in situ hybridization (FISH) may be applied, possibly in combination with PCR-DGGE. Moreover, FISH may enable a fast detection and determination of relative abundances of specific bacterial cells in a mixed bacterial culture and be used to study the interaction between the MTBE degrading species. In particular embodiments, the methods for the identification of the strains *Methylibium* LD3, *Hydrogenophaga* LD1 and/or *Mycobacterium* LD6 involve the identification of a strain-specific 16S rRNA sequence.

Thus, the present invention further relates to methods for detecting the presence of a *Methylibium* LD3, *Hydrogenophaga* LD1 and/or *Mycobacterium* LD6 micro-organism in a sample comprising identifying the presence of a sequence corresponding to SEQ ID NO:1, SEQ ID NO:2 or SEQ ID NO:3, respectively in said sample. The term 'sample' as used herein refers to a specimen or small quantity of material studied, i.e. a small quantity of medium possibly contaminated with MTBE, TBA and/or HCHO. As indicated above, in order to identify the sequences corresponding to SEQ ID NO:1, SEQ ID NO:2 and/or SEQ ID NO:3, 16S rRNA sequences of the bacteria present in the sample may be amplified using 16S rRNA specific primers and PCR-DGGE analysis performed. In this way, the obtained 16S rRNA gene DGGE fingerprint or signature may indicate dominant bands in the 16S rRNA gene profile which may be used to identify the bacteria present in the sample. One isolate or several isolates may hereby be identified. Alternatively, or in combination with the steps described above, the 16S rRNA sequences of the bacteria may be cloned and/or sequenced to determine their polynucleotide composition. The obtained polynucleotide sequence may be used in alignment studies to identify the bacteria and possibly to analyze their phylogenetic relationship. For sequence comparison, typically one sequence acts as reference sequence to which test sequences are compared. Methods of sequence alignment are well-known in the art. Preferably, for nucleic acids sequence comparison the BLAST algorithm is used. Using the BLAST algorithm sequence identity and sequence similarity may be determined and examples of algorithms that can be used are described in Altschul et al. (1990) J. Mol. Biol. 215:403-410. Software for performing BLAST analysis is publicly available through the National Center for Biotechnology Information (www.ncbi.nlm.nih.gov/). Manual inspection and correction of the alignment and phylogenetic analysis may be performed using ARB (Ludwig et al. 2004, Nucleic Acids Research 32(4):1363-1371). Analysis of multiple sequence alignments of the 16S rRNA sequences represented by SEQ ID NO:1, SEQ ID NO:2 and/or SEQ ID NO:3 with 16S rRNA sequences present in public databases permits the design of oligonucleotide primers (and probes) capable of amplifying (or hybridizing) segments of 16S rRNA genes of a wide or limited variety of bacterial species.

In particular, according to the present application, the method of the present invention for detecting the presence of a *Methylibium* LD3, *Hydrogenophaga* LD1 and/or *Mycobacterium* LD6 micro-organism in a sample may comprise a step of contacting said sample with a primer or probe capable of hybridizing specifically to or amplifying a sequence specific for SEQ ID NO:1, SEQ ID NO:2 or SEQ ID NO:3 and determining the presence of a hybridization signal or an amplification product indicative of the presence of *Methylibium* LD3, *Hydrogenophaga* LD1 and/or *Mycobacterium* LD6 in the sample. Methods to perform DNA extraction, hybridization, amplification, sequencing and sequence comparison are well known by a person skilled in the art and may be easily adapted according to the specific condition. The probes or primers used may be radio-labeled, fluorescent, or even coupled to an enzyme.

Preferably, the probes and/or primers hybridize under stringent hybridization conditions to polynucleotides present in the strains of the present invention. In particular, the probes or primers hybridize under stringent conditions to sequences represented by SEQ ID NO:1, SEQ ID NO:2 or SEQ ID NO:3. 'Stringent hybridization conditions' may be defined as conditions that enable specific hybridization of two single-stranded DNA molecules at about 65° C., for example in a solution of 6×SSC, 0.5% SDS, 5×Denhardts solution and 100 µg/ml of denaturated unspecific DNA, or any other solution of equivalent ionic strength, and after a washing step performed at 65° C., for example in a solution of at most 0.2×SSC and 0.1% SDS, or a solution of equivalent ionic strength. However, the stringency conditions can be adapted by the skilled in the art, depending on the size of the hybridizing sequence, its GC content and any other parameter, for example according to the protocols that are described by Sambrook et al. 2001 (Molecular Cloning: A Laboratory Manual, $3^{rd}$ Ed., laboratory press, Cold Spring Harbor, N.Y.). The probe and/or primer may be a 'nucleotide fragment' longer than 10 nucleotides, preferably longer than 20 nucleotides, and even more preferably longer than 50 nucleotides. The sequence of the primers and/or probes is, or is fully complementary to, the sequence represented by SEQ ID NO:1, SEQ ID NO:2 or SEQ ID NO:3.

The present invention further relates to isolated polynucleotide sequences comprising or consisting of the sequence represented by SEQ ID NO:1, SEQ ID NO:2 or SEQ ID NO:3. The term 'isolated' or 'purified' used in this context referring to a nucleotide sequence refers to material that is substantially or essentially free of other compounds that are normally present in its natural environment, such as but not limited to other DNA sequences. Purity of a polynucleotide is typically determined using analytical techniques such as polyacrylamide gel electrophoresis. The term 'isolated' or 'purified' denotes that a nucleic acid sequence generates one band in an electrophoretic gel. In particular, it means that the nucleic acid is at least 85% pure, more preferably at least 95% pure, and most preferably at least 99% pure. The term 'nucleic acid' or 'polynucleotide' refers to deoxyribonucleosides or ribonucleosides and polymers thereof in either single- or double-stranded form. The term encompasses nucleic acids containing known analogs or modified backbone residues or linkages. Examples of such analogs include, without limitation, phosphorothioates, phosphoramidates, methyl phosphonates, chiral-methyl phosphonates, 2-O-methyl ribonucleotides, peptide-nucleic acids (PNAs). A particular nucleic acid sequence may also encompass conservatively modified variants thereof (e.g. degenerate codon substitutions) and complementary sequences, as well as the sequence explicitly indicated. In particular embodiments as described above, the isolated nucleic acids are suitable for use in the detection of the bacterial strains described herein.

In addition, the present invention relates to kits for detecting and identifying the presence of a *Methylibium* LD3, *Hydrogenophaga* LD1 and/or *Mycobacterium* LD6 strain, or a consortium comprising one or more of said strains in a sample. In particular embodiments, the kits according to the present invention comprise one or more primer pairs or probes capable of hybridizing specifically to or amplifying a sequence specific for SEQ ID NO:1, SEQ ID NO:2 and/or SEQ ID NO:3. The invention also concerns probes and/or primers specific for the consortium, methods and biosensors for identifying the presence in a medium or sample of a bacterium of the present invention and, if necessary, for isolating such microorganisms.

In yet a further aspect, the present invention provides isolated bacterial strains useful in the degradation of MTBE, TBA and/or HCHO.

Thus, the present invention also relates to an isolated methyl-tertiary-butyl-ether (MTBE) degrading *Methylibium* strain, which corresponds to strain *Methylibium* LD3, deposited as LMG P-27480. This strain is characterized by the presence of 16S rRNA sequence SEQ ID NO:1.

The present invention further provides an isolated TBA degrading strain which corresponds to strain *Hydrogenophaga* LD1 deposited as LMG P-27479 which is characterized by the presence of 16S rRNA sequence SEQ ID NO:2.

The present invention further provides isolated HCHO degrading strain *Mycobacterium* LD6 deposited as LMG P-27498 which is characterized by the presence of 16S rRNA sequence SEQ ID NO:3.

The isolated strains according to the present invention can further be genetically modified to include a heterologous polynucleotide sequence. Bacteria comprising a heterologous polynucleotide are referred to as recombinant bacteria. The term 'heterologous' refers to a sequence that is not found in the cell or microorganism in nature. For example, the recombinant bacterium may comprise a heterologous sequence responsible for (or increasing) the degradation of MTBE, TBA, HCHO or other (ether) fuel contaminants. In particular embodiments, the heterologous DNA sequence comprises a gene under control of a promoter. Additionally or alternatively the recombinant bacteria according to the present invention may comprise a reporter gene, a resistance gene and/or a susceptibility gene. The reporter and/or resistance gene can be used for detection of the strain. For instance, the heterologous gene may help identify the strains of the present invention when added to a medium. Suitable reporter genes include any reporter protein known in the art, for example a bioluminescent protein such as luciferase or an enzyme such as peroxydase or beta-galactosidase. Means to reveal the expression of such reporter genes are known by the skilled artisan. Additionally or alternatively, a susceptibility gene may be used to prevent uncontrolled spread of the recombinant bacteria in the environment, e.g. by the addition of a product that will selectively kill the bacteria carrying the susceptibility gene.

The present invention will now be further illustrated by means of the following non-limiting examples.

EXAMPLES

Example 1: Stability of MTBE-Degrading Properties of the M-Consortium

The M-consortium was enriched from a soil sample by regular feeding with pure oxygen and MTBE and occasional transfer to fresh mineral medium (WXP, pH 7.1). Standard WXP medium (pH 7.1) contained 8.8 g/L $Na_2HPO_4.2H_2O$, 3 g/L $KH_2PO_4$, 1 g/L $(NH_4)_2SO_4$, 0.2 g/L $MgCl_2.6H_2O$, 0.1 g/L $Ca(NO_3)_2.4H_2O$, 4 mg/L Na-EDTA, 1.5 mg/L $FeCl_2$, 50 µg/L $MnCl_2.4H_2O$, 20 µg/L $CoCl_2.6H_2O$, 15 µg/L $NaMoO_4.2H_2O$, 10 µg/L $ZnCl_2$, KBr and KI, 5 µg/L $CuSO_4$ and $H_3BO_3$ and 2.5 µg/L LiCl, $SnCl_2.2H_2O$ and $BaCl_2$.

The stability of the MTBE-degradation capacity of M-consortium culture was evaluated by transferring 5 ml of a soil free culture in sterile 250 ml vials containing 120 ml WXP medium, 1.3 g yeast extract (0.1%) and 8 µg MTBE. The flasks were sealed with butyl rubber stoppers and incubated on a rotary table (100 rpm). Incubation conditions were pH 7.1, 10 mg/L dissolved oxygen and 30° C. The cultures received regular spikes of 8 µg MTBE through the butyl rubber stoppers of the vials using 10 µL Hamilton glass syringes (Hamilton, Bonaduz, Switzerland). Also pure oxygen (10-30 ml) was regularly added via a syringe through the stoppers. MTBE (50 mg/L, HPLC grade, Sigma-Aldrich, Bornem, Belgium) and TBA (analysis grade, Merck, Darmstadt, Germany) concentrations were measured by head space analysis of 5 mL samples supplied with 2 g/L $NaN_3$ (to stop the reactions), by CC-MS using a Trace CC Ultra gas chromatograph (Thermo Electron Corporation, Cambridgeshire, United Kingdom) fitted with a DSQ massspectrometer (Thermo Electron Corporation) and equipped with a HP-VOC column (30 m length, 0.20 mm inner diameter and 1.12 µm film thickness, Agilent technologies, Diegem, Belgium) and split/splitless injection. Calibration was performed in the 0-5000 µg/L range using d6-benzene, d10-ethylbenzene and dibutylether as internal standards. Detection limits were 2 µg/L MTBE and 65 µg/L. pH was measured using a pH electrode (Hanna Instruments, IJsselstein, The Netherlands) and dissolved oxygen concentrations using a flow through electrode (Si Strathkelvin instruments, Namen, Belgium).

Figure 1:
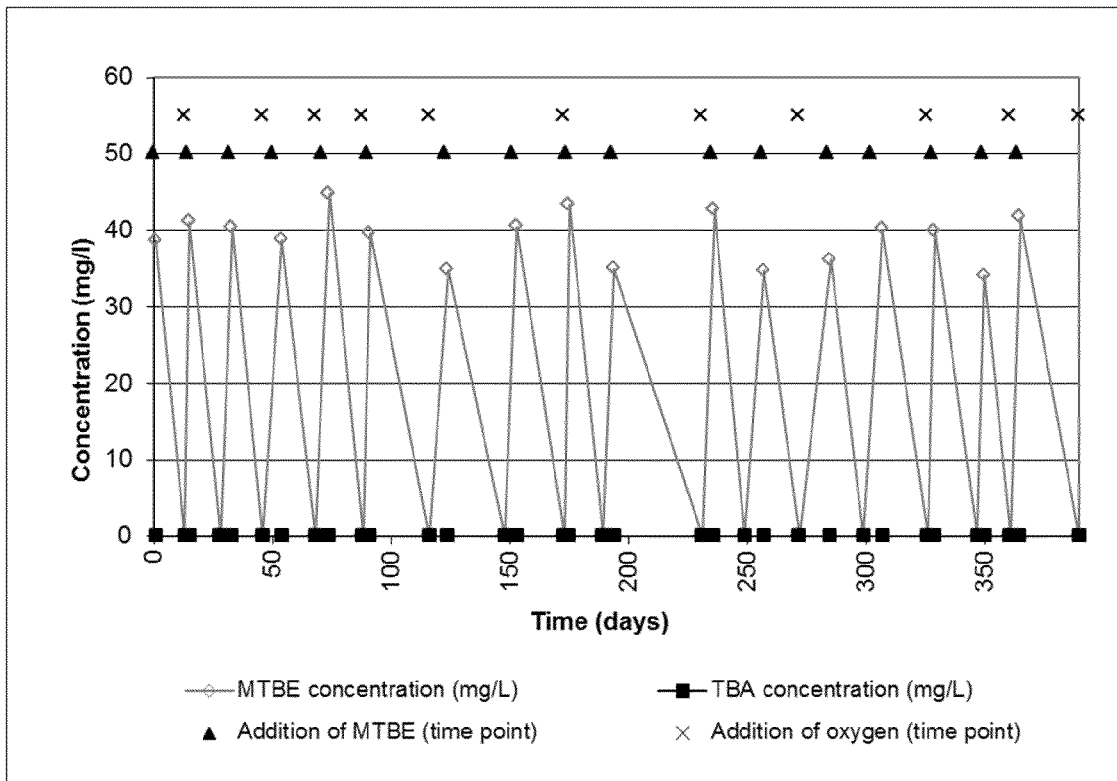
FIG. 1 illustrates growth on and degradation of either 50 mg/L MTBE (a), TBA (b), HIBA (c) or HCHO (d) by the M-consortium according to an embodiment envisaged herein.
Figure 1:
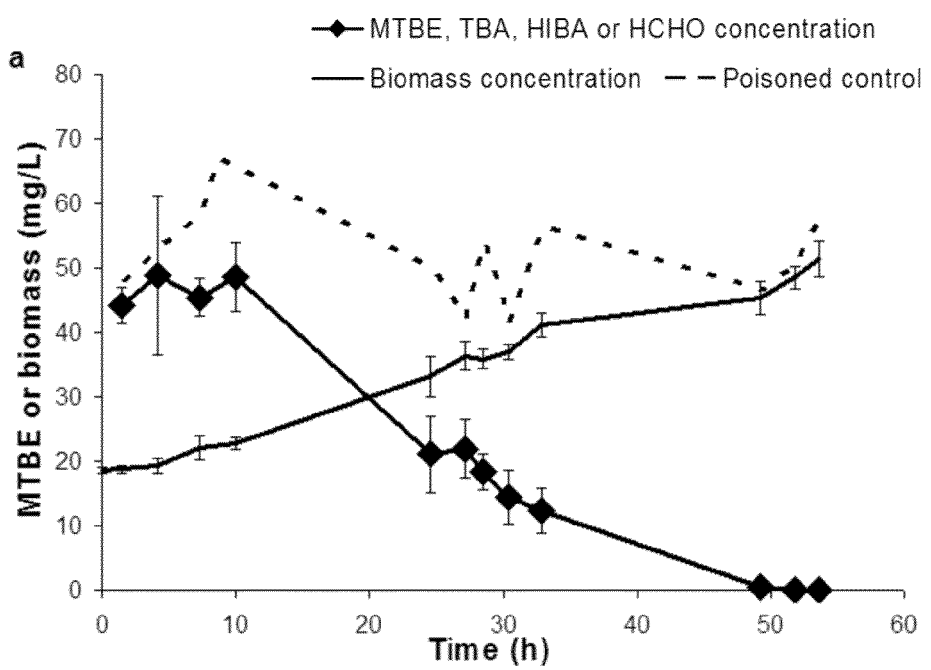

FIG. 1 displays the evolution of the MTBE-concentration in a flask inoculated at day 1 with the M-consortium, and indicates that for more than 350 days each spike of MTBE was completely degraded without accumulation of TBA. The oxygen concentration fluctuated between 10 mg/l and 1 mg/L, while the pH decreased slightly from pH 7.1 to pH 6.7.

The M-consortium has been preserved for more than ten years by regular feeding with pure oxygen and MTBE and occasional transfer to fresh mineral medium (WXP, pH 7.1). The M-consortium stock culture was routinely grown in glass recipients like 1 L bottles filled with 0.5 L standard mineral medium (WXP). The flasks were sealed with butyl rubber stoppers and incubated horizontally on a rotary table (100 rpm). Incubation conditions were pH 7.1, 10 mg/L dissolved oxygen and 20° C. The cultures received regular spikes of 40 to 50 mg/L MTBE and 60 mL of pure oxygen through the butyl rubber stoppers of the vials.

Example 2: Degradation Tests with M-Consortium and Calculation of Kinetic Constants Parallel cultures of the M-consortium with an initial concentration of 50 mg/L MTBE, TBA, HIBA or HCHO were set up in order to record the growth rate and the biomass yield and to examine changes in the microbial community structure in function of time. The M-consortium culture was transferred from the stock solution (see example 1) to triplicate batch flasks containing WXP with either 50 mg/L MTBE, TBA, HIBA or HCHO. MTBE can be converted to TBA and HCHO; HIBA (2-hydroxyisobutyric acid) is a degradation product of TBA. For each carbon source, the evolution of MTBE, TBA, HIBA and HCHO and biomass concentration was measured in function of time until the substrate concentrations were under the detection limit. A poisoned control (2 g/L $NaN_3$) was included for every test condition.

MTBE, TBA, pH and oxygen were measured as described in example 1. HIBA (98%, Acros Organics, Geel, Belgium) was measured in solution in cell free samples using HPLC (series 1200, Alltech Technologies, Lokeren, Belgium) equipped with an Alltech OA 1000 Organic Acids column and a UV-VIS detector (Hitachi L-4250, Merck) at 214 nm, with 17.5 mM $KH_2PO_4$ and 1N $H_2SO_4$ (pH 2.5) used as carrier at 0.8 mL/min and with a detection limit of 2 mg/L. HCHO (37% with about 10% methanol, analysis grade, Merck) was measured in cell free samples, based on a standard curve of 0-60 mg/L HCHO solutions measured in triplicate. The detection limit was 0.2 mg/L HCHO. Biomass concentration was measured as optical density at 660 nm wavelength ($OD_{660}$) with a spectrophotometer (Amersham Pharmacia Biotech, Roosendaal, The Netherlands). Optical density was converted to dry weight of biomass (DW) through a correlation of 1 $OD_{660}$=390.14+/−3.79 mg DW/L ($R^2$=0.95), based on various independent triplicate measurements of $OD_{660}$ in function of volatile suspended solids with a range of 0.001-0.5 $OD_{660}$.

The specific biomass growth rate (1/h) was calculated by means of a linear regression of the natural logarithm of the measured biomass concentration (mg DW/L) in function of time, thus assuming exponential growth and a maximal specific biomass growth rate. The biomass yield (mg DW/mg carbon source) was determined using the ratio of the measured increase in biomass concentration (mg DW/L) to the measured decrease in carbon source concentration (mg/L). An average value and a 95% confidence range for the triplicate experiments were calculated using Excel.

RESULTS: The M-consortium grew on 50 mg/L MTBE, TBA, HIBA and HCHO as the only source of carbon and energy (FIG. 2 and Table 1). A temporary build-up of TBA was measured during MTBE degradation. No accumulation of HIBA or HCHO was measured in the MTBE grown cultures (data not shown). The M-consortium grew on TBA and HIBA with biomass doubling times of less than one day, whereas growth on MTBE and HCHO was slower, with doubling times of about 1.5 days. The biomass yield on MTBE and TBA was 0.5 mg DW/mg MTBE and 0.6 mg DW/mg TBA, respectively, whereas the yield on HIBA and HCHO was lower, i.e., 0.28 mg DW/mg HIBA and 0.12 mg DW/mg HCHO, respectively (Table 1). No increase of the optical density was measured after degradation of one spike of 50 mg/L HCHO (FIG. 2(d)). Therefore, the growth rate and the biomass yield on HCHO were calculated based on the growth of an enrichment culture grown on 7 spikes of 50 mg/L HCHO for 75 days.

TABLE 1

Recorded growth rates and biomass yields of the M-consortium cultured on either 50 mg/L MTBE, TBA, HIBA or HCHO.

| Carbon source | Growth rate (1/h) | Biomass yield (g DW/g carbon source) |
|---|---|---|
| MTBE | 0.018 ± 0.003 | 0.50 ± 0.04 |
| TBA | 0.030 ± 0.001 | 0.60 ± 0.002 |
| HIBA | 0.034 ± 0.001 | 0.28 ± 0.01 |
| HCHO | 0.017 ± 0.002 | 0.12 ± 0.03[a] |

[a] The calculated biomass yield on HCHO is based on a culture which received 7 spikes of 50 mg/L HCHO (no significant growth during degradation of 1 × 50 mg/L).

Example 3: Identification of the Key Organisms in the MTBE/TBA Degrading M-Consortium Parallel to example 1, duplicate cultures of the M-consortium were grown in liquid WXP containing either 50 mg/L MTBE, TBA, HIBA or HCHO for 75 days. Growth of the cultures was monitored daily and every sample was measured for pH and dissolved oxygen concentration. If necessary, pure oxygen was provided into the head space to restore saturated conditions in solution. The cultures were regularly checked for accumulation of carbon source or intermediates, i.e., MTBE, TBA, HCHO and HIBA. When the compounds were depleted, new carbon source was added. After 75 days, the cultures were plated for isolation of bacterial strains (see example 4) and DNA was extracted from the cells for 16S rRNA gene based molecular analyses analysis.

DNA was extracted from the different M-consortium cultures and dissolved in TE buffer (10 mM This, 1 mM EDTA, pH 8.0 with HCl). To amplify part of the bacterial 16S rRNA gene (El-Fantroussi et al., 1999, Appl. Env. Microbiol. 65:982-988), the PCR mixture consisted of 5 µL 10× buffer solution, 4 µl dNTPs solution, 0.25 µL Taq polymerase (TaKaRa Bio Inc., Shiga, Japan), 0.25 µL of primer 518R, 0.5 µL for primer GC-63F, 1 µL of DNA extract and 39 µL of PCR water. PCR was performed in a T3 Thermocycler (Biometra, Goettingen, Germany). The PCR products were first analysed by agarose gel electrophoresis (1.5% (w/v), 85V) for 1 h, stained with 0.01% GelRed (v/v) (VWR, Leuven, Belgium) and photographed under UV light using a digital camera system with image software (Image Master VDS & Liscap Image Capture 1.0, Pharmacia Biotech). The PCR products were then analysed by DGGE using an 8% polyacrylamide gel in 1× Tris-acetate-EDTA buffer (BioRad, Nazareth, Belgium), with a denaturing gradient of 35% to 65% as described by Muyzer et al. (1993, Appl. Environ. Microbiol. 59:695-700), using an Ingeny phorU-2DGGE apparatus (Ingeny International, Goes, The Netherlands). The gels were run for 15 h at 60° C. and 120V, stained with 0.01% GelRed (v/v) (VWR, Leuven, Belgium) and photographed as described above.

The 16S rRNA gene was amplified and cloned using specific primers according to Lane (1991, Nucleic Acids techniques in Bacterial Systematics pp. 115-147 John Wiley & Sons, Chichester). The 16S rRNA gene fragments were cloned into the pCR2.1-TOPO vector, using the TOPO TA Cloning kit according to the instructions of the manufacturers (Invitrogen, Carlsbad, USA). The insert of a single colony was analysed using primers M13F/M13R (Invitrogen), followed by PCR-DGGE analysis of the partial bacterial 16S rRNA gene fingerprint using primers GC63F/518R. Plasmid DNA was extracted from selected clones using a Qiagen Plasmid Midi Kit, according to the instructions of the manufacturers (Qiagen, Venlo, The Netherlands). Sequencing was carried out by the BCCM/LMG Bacteria Collection (27-1492 sequence, Ghent, Belgium) or by the VIB Genetic Service Facility (partial sequences, Wilrijk, Belgium). Comparison of 16S rRNA gene sequences retrieved from the M-consortium and the GenBank nucleotide sequence database was performed using BLAST. ARB-silva was used for alignment of the nearly-full-length 16S rRNA gene sequences of the consortium and the nearest neighbours. Manual inspection and correction of the alignment and phylogenetic analysis was performed using ARB.

RESULTS: The 16S rRNA gene pool present in the M-consortium was analysed using cloning and sequencing of the isolated 16S rRNA genes. This was performed four times for cultures grown on MTBE, over a period of two years, whereas for the cultures on TBA, HIBA and HCHO, this was performed once. Seven different 16S rRNA gene sequences (<80% sequence similarity) showing different DGGE profiles were recovered from the cultures grown on either MTBE, TBA, HIBA or HCHO.

In total, 64 clones were recovered from cultures growing on MTBE. Of these clones, 52 showed a 16S rRNA gene profile with a single band corresponding to the dominant band F/G/H recorded in the DGGE community profile of the MTBE grown culture. Five of these clones were sequenced. All 5 sequences were identical and showed the highest similarity to the 16S rRNA gene sequence of a bacterium belonging to the genus *Hydrogenophaga*, i.e., *Hydrogenophaga* sp. Rs71. The clone representing this sequence was designated clone MTBE1.

The 16S rRNA sequence represented by clone MTBE2 showed the highest similarity to the 16S rRNA gene sequence of an unpublished uncultured bacterium (GenBank accession number EF664640, unpublished). The 16S rRNA sequence recovered from clone MTBE3 had a 16S rRNA gene sequence similar to this of *Thermomonas* sp. ROi19. Clone MTBE2 and MTRE3 apparently represented non dominant bands in the community DGGE profile of the MTBE grown cultures.

From the cultures grown on TBA, 18 clones were recovered. All those clones showed the same DGGE profile as clone MTBE1 which was derived from the MTBE grown cultures and the 2 sequenced clones had an identical 16S rRNA gene sequence. The clone representing these sequences was designated clone TBA1.

The bacterial 16S rRNA gene sequence of the two clones (HIBA1 and HIBA2) were almost identical to each other (99%) and showed the highest similarity to the 16S rRNA gene sequence of a bacterium belonging to the genus Raistonia, i.e., *Ralstonia* sp. K401.

From the cultures grown on HCHO, 4 sequences were recovered, represented by clones HCHO1, HCHO2, HCHO3 and HCHO4. Clones HCHO3 and HCHO4 were identical to clone HIBA1 and clone HIBA2 recovered from the HIBA grown culture, respectively. Clone HCHO1 and clone HCHO2 were both related to unpublished α-Proteobacteria, based on the partial 16S rRNA gene sequences (Table 2).

Example 4: Isolation of Pure Bacterial Strains from the M-Consortium

Two approaches were used to isolate pure bacterial strains from the consortium. On the one hand, plating onto R2A medium (15 g/L agar) of serial dilutions of the M-consortium which was enriched for 75 days on either 50 mg/L MTBE, TBA, HIBA or HCHO as described in example 3. R2A medium (pH 7.0) contained 0.5 g/L protease peptone, yeast extract, casein hydrolysate, D+ glucose and starch, 0.3 g/L sodium pyruvate and $K_2HPO_4$ and 0.1 g/L $MgSO_4 \cdot 7H_2O$. The agar plates were incubated at 20° C. for at least 21 days before the colonies were picked up and analysed. On the other hand, isolates were obtained by plating the M-consortium on WXP mineral medium agar plates containing MTBE, TBA, HCHO or HIBA as the only carbon source, using a saturated MTBE or TBA atmosphere or at concentrations in the agar of 50 mg/L TBA, HCHO or HIBA, incubating the plates at 29° C. for at least 48 days. Single colonies were picked up and purified by transfer on R2A medium. The 16S rRNA gene fingerprint was determined with PCR-DGGE as described in example 3. The isolates were stored in $10^{-2}$ M $MgSO_4$ at 4° C. and in glycerol (15% v/v) and 0.85% (w/v) NaCl at −20° C. Before use, they were checked for purity on R2A plates and for the right PCR-DGGE profile. PCR with primers targeting genomic repetitive elements present in the DNA of pure cultures was used to obtain a fingerprint of the bacterial genome. The primers used were BOX A1R, REP2 and REP1R or ERIC2 and ERIC-1R, according to Versalovic et al. (1991, Nucl. Acids Res. 19:6823-6831) and Versalovic et al. (1994, Meth. Mol. Cell. Biol. 5:25-40). The PCR products were analysed with a 1% (w/v) agarose gel at 180V for 4 h and photographed as described before.

Plating of the MTBE grown M-consortium on R2A plates resulted in 4 isolates (LD1, LD4, LD5 and LD7). Isolate LD1 and isolate LD4 formed bright yellow and dark yellow colonies on R2A agar plates, respectively. Isolate LD5 formed bright white colonies, with a characteristic red margin and center. Isolate LD7 formed bright white colonies on R2A medium. Isolate LD2 and LD3 were isolated from the MTBE grown culture using WXP plates that were incubated under a MTBE and an TBA atmosphere for 48 days, but were also picked up from WXP plates without carbon source. These strains grew slowly on WXP agar plates with and without MTBE and on R2A plates and formed white (LD2) and yellowish (LD3) colonies on all plates. Isolate LD6 was isolated on WXP plates containing 50 mg/L HCHO. This bacterium was not present on WXP plates containing MTBE, TBA or HIBA. Isolate LD6 formed white colonies with irregular margins on R2A. No additional bacterial strains to those isolated from the MTBE-grown cultures could be isolated from the cultures grown on TBA, HIBA or HCHO using R2A plates and WXP agar plates. Isolate LD4 was only found in the MTBE-grown cultures and the HCHO-grown culture contained only isolates LD2 and LD6.

The bacterial species composition of the M-consortium based on plating in function of time changed during the study. Initially, isolate LD4 and LD5 dominated the plates grown from the MTBE cultures and to a lesser extent, isolate LD7 and LD1 were found. At the end of the study (after two years), isolates LD3 and LD1 were selectively enriched in the M-consortium and were found in the highest numbers on the R2A plates.

DNA was extracted from a pellet of an overnight-grown culture of the isolates in liquid R2A and processed as described in example 3. Sequencing of the 16S rRNA genes amplified from the isolates showed that isolates LD1 and LD5 were the isolates represented in the community 16S rRNA gene pool by clones MTBE1 and MTBE3, respectively, previously obtained from the MTBE and the TBA grown cultures. The identical 16S rRNA gene of the respective clones and isolates was confirmed by the identical 16S rRNA gene DGGE profile (data not shown). Based on the nearly-full-length 16S rRNA gene sequence, isolates LD1 and LD5 were identified as a *Hydrogenophaga* species and a *Thermomonas* species, respectively. The 16S rRNA gene of isolate LD7 was not sequenced but isolate LD7 could be associated with clone HIBA1 and HIBA2 by bacterial 16S rRNA gene PCR-DGGE profiling (data not shown). The information that the genome of *Ralstonia* spp. contains 4 rRNA gene copies supports the hypothesis that isolate LD7 is a *Ralstonia* strain. The 16S rRNA gene sequence of isolate LD4 was not determined. BOX, ERIC and REP genome fingerprints of *Methylibium* sp. LD3 were compared to those generated for the MTBE and TBA degrading PM1 (data not shown). The results indicated that the strains have different genomic profiles and hence that isolate *Methylibium* sp. LD3 and *M. petroleiphilum* PM1 are different bacterial strains of the genus *Methylibium*.

Sequences of the 16S rRNA genes of *Methylibium* sp. LD3, *Hydrogenophaga* sp. LD1 and *Mycobacterium* sp. LD6 are shown in FIGS. 3-5, respectively.

Deposits:

*Methylibium* LD3, *Hydrogenophaga* LD1 and/or *Mycobacterium* LD6 strains were deposited as deposit under the Budapest Treaty by the Belgian Co-ordinated Collections of Micro-organisms (BCCM/LMG) Department of Molecular Biology, Ghent University, K. L. Ledeganckstraat 35, 9000 Gent, Belgium on 28 February, and 29 March (for LD6) 2013 by Dirk Fransaer, representative of VITO and were attributed deposit numbers LMG P-27480, LMG P-27479 and LMG P-27498, respectively. The M-consortium was deposited as deposit under the Budapest Treaty by the Belgian Co-ordinated Collections of Micro-organisms (BCCM/LMG) Department of Molecular Biology, Ghent University, K. L. Ledeganckstraat 35, 9000 Gent, Belgium on 3 Oct. 2013 by Dirk Fransaer, representative of VITO and was attributed deposit number LMG P-27909. All restrictions on access to deposit LMG P-27480 will be irrevocably removed at the time a patent issues in the United States on the basis of this application.

Example 5: Degradation Capacities of the Pure Cultures Isolated from the M-Consortium All obtained isolates except *Ralstonia* sp. LD7 were assessed for growth by degradation of 50 mg/L MTBE, TBA, HIBA and 20 or 50 mg/L HCHO in mineral medium. The isolates were grown on liquid R2A, washed twice with $10^{-2}$ $MgSO_4$ and tested for degradation of 50 mg/L MTBE, 50 mg/L TBA, 50 mg/L HIBA and 20 or 50 mg/L HCHO in 1 L bottles as described above for the consortium (example 2).

The isolated *Methylibium* sp. LD3 degraded and grew on 50 mg/L MTBE (FIG. 6a), TBA (FIG. 6b) and HIBA and on 20 mg/L HCHO but not on 50 mg/L HCHO. *Hydrogenophaga* sp. LD1 degraded and grew on 50 mg/L TBA (FIG. 6c) and HIBA and on 20 mg/L HCHO, but not on 50 mg/L MTBE or HCHO. *Mycobacterium* sp. LD6 degraded and grew on 20 to 80 mg/L HCHO (FIG. 6d) but not on MTBE, TBA or HIBA. However, *Methylibium* sp. LD3 stopped growing during MTBE degradation at an optical density of about 0.12. The TBA concentration in this culture remained below the detection limit of 0.06 mg/L during the whole experiment period, whereas the HCHO concentration slightly increased up to 0.42 mg/L at the end of the experiment. The other isolates did not grow on or degrade any of the tested compounds. *Hydrogenophaga* sp. LD1 and *Mycobacterium* sp. LD6 were additionally tested for co-metabolic degradation of MTBE by incubation with 50 mg/L MTBE, mixed with 0.01% (w/v) yeast extract (YE) or 50 mg/L MTBE mixed with 50 mg/L TBA for *Hydrogenophaga* sp. LD1 or 50 mg/L HCHO for *Mycobacterium* sp. LD6. The cultures did not degrade MTBE, whereas yeast extract and the respective carbon sources TBA and HCHO were rapidly removed.

Example 6: Relative Abundance of Key-Isolates within the M-Consortium

Figure 7:
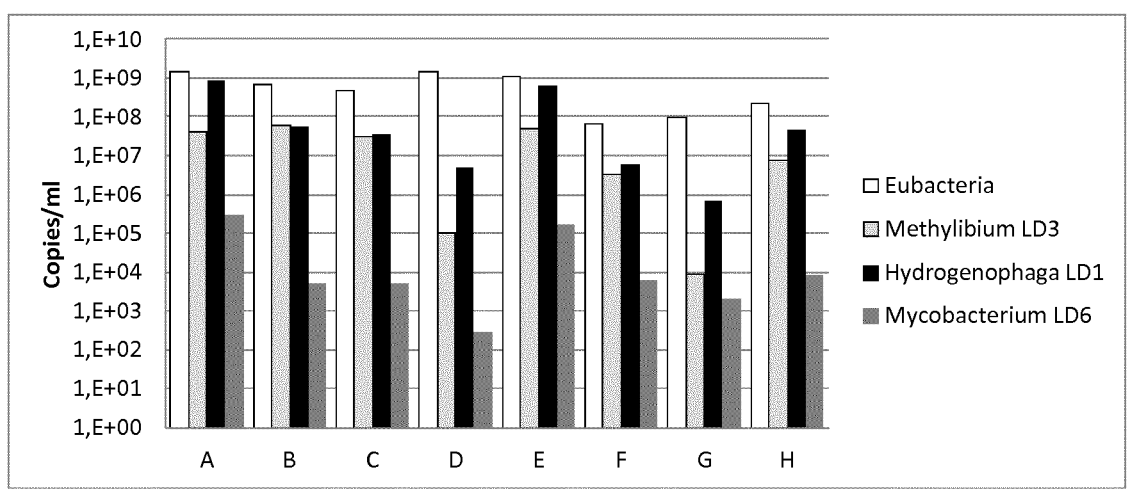
FIG. 7 illustrates the absolute abundance of *Methylibium* sp. LD3, *Hydrogenophaga* sp. LD1, *Mycobacterium* sp. LD6 in different growth cultures of the M-consortium taken over time, as determined via Quantitative Polymerase Chain Reaction (qPCR) using specific primers targeting the 16SrRNA gene of *Methylibium* sp. LD3, *Hydrogenophaga* sp. LD1, *Mycobacterium* sp. LD6.

Based on the 16S rRNA gene sequences displayed in FIGS. 3 to 5, specific qPCR primers were developed and used to determine the abundance of *Methylibium* sp. LD3, *Hydrogenophaga* sp. LD1 and *Mycobacterium* sp. LD6 in M-consortium cultures; FIG. 7 shows results for 8 different M-consortium stock cultures (see example 1). The absolute concentration of *Methylibium* LD3, *Hydrogenophaga* LD1 and *Mycobacterium* LD6 in examined M-consortium cultures was between $10^4$-$10^8$ copies per ml, $10^6$-$10^9$ copies/ml and $10^2$-$10^6$ copies/ml, respectively.

Figure 8:
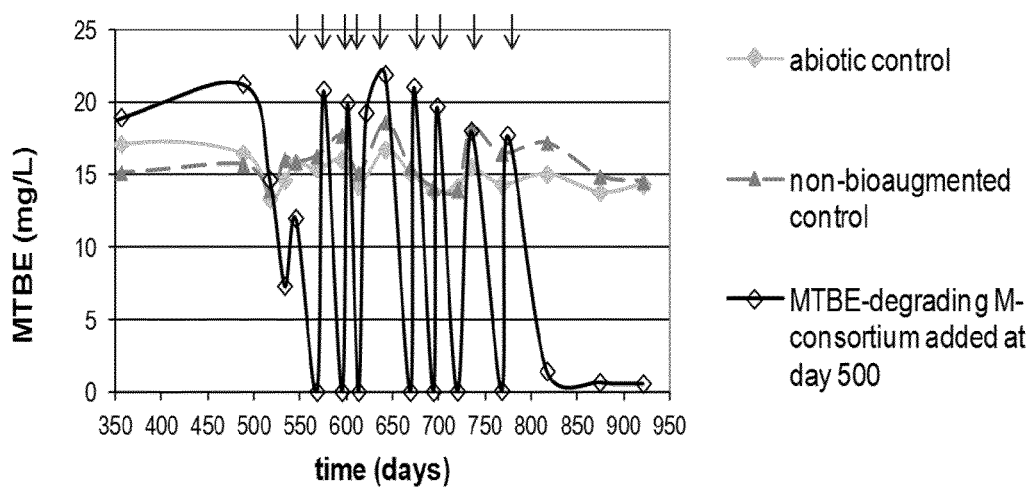
FIG. 8 illustrates the stable MTBE-degradation characteristics of the M-consortium in non-sterile environmental matrices comprising aquifer material and groundwater from a real contaminated. The arrows depict the time of the addition of MTBE.

Example 7: M-Consortium as Inoculum for Pollutant Removal from Contaminated Soil and Groundwater Batch-degradation experiments were set up under aerobic conditions in closed 120 ml serum vials with aquifer materials (75 g) from an MTBE-contaminated site and a mineral medium (145 ml) described by Mo et al. (1997, Apppl. Microbiol. Biotechnol. 47:69-72). 150 µL of pure MTBE was spiked through the septa, resulting in a final concentration of 15 mg/L. The cultures were incubated at 20° C. The evolution of the MTBE concentration in an abiotic control and in the tests vials was followed in time, as also the pH and the dissolved oxygen concentration (see example 1). However, no degradation of MTBE was obtained during an experimental time of more than 2 years (FIG. 8). After about 500 days of incubation, 2.6 $10^8$ viable cells of the M-consortium were added to some test vials. After addition of the inoculum, the MTBE-concentration decreased within a few weeks from 15 mg/l to below 10 µg/l (FIG. 8), while no decreases in MTBE-concentration were observed in the non-inoculated conditions. The inoculated batch tests continued degrading re-additions of the MTBE during more than 1 year, without the need for addition of additional M-consortium. This result indicates that no inhibiting factors were preventing MTBE-degradation at the site, but rather the lack of suitable micro-organisms. The M-consortium was also successfully used as inoculum to stimulate MTBE-degradation in similar tests with different soil types (sand, loamy sand, . . . ).

Figure 9:
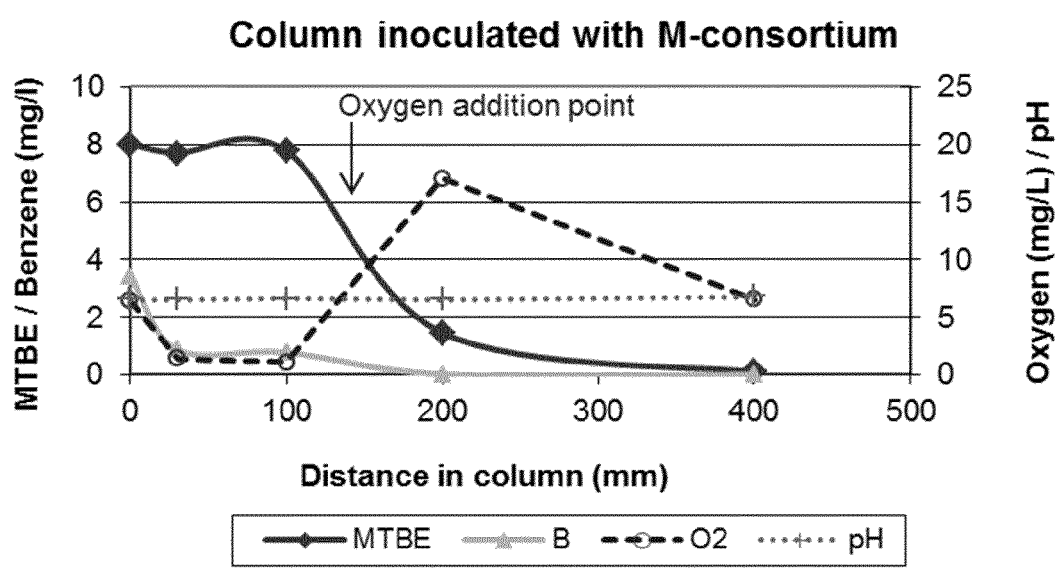
FIG. 9 illustrates the removal of MTBE and benzene from a (ground)water while passing at a velocity of 50 cm/day through columns (L=50 cm) filled with carrier material inoculation with the M-consortium.

To evaluate M-consortium as inoculum in continuous systems, Plexiglas columns (diameter 4 cm, length 50 cm) were filled with different carrier materials. (perlite, aquifer material, filter sand and polymer beats) and inoculated with the M-consortium (±6 $10^{10}$ cfu/column). Non-inoculated columns were set-up in parallel as controls. Artificial groundwater (diluted minimal mineral medium), polluted with MTBE (10-40 mg/l) only or in combination with BTEX-compounds (5 mg/l benzene), was pumped through the columns bottom-up. The hydraulic Retention Time (HRT) in the columns was 1 to 2 days depending on the filling material. Along the columns sampling points were present at different distances from the entrance (bottom of the columns), which allowed the determination of pollutant concentration profiles as well as the evolution of pH en dissolved oxygen concentration (DO) along the columns. Extra oxygen was added to the aerobic column (influent & at 15 cm from the entrance) systems via a diluted solution of hydrogen peroxide using a syringe pump (final concentration <0.01%). The major part of the benzene was rapidly degraded in the inoculated as well as the non-inoculated columns. On the other hand, MTBE was only removed from the water when the M-consortium was present (FIG. 9—filter sand). In general, in the presence of benzene a delay of the MTBE-degradation was seen as shown in FIG. 2.C. During this delay the BTEX-compounds were degraded, consuming the available oxygen. Once the BTEX-compounds were degraded and sufficient oxygen remained or was added, the MTBE-degradation started. No significant accumulation of TBA was observed.

After 11 months of operation, all 13 columns were dismantled. The biomass in different fractions of the columns was quantified via measurement of the protein concentration. The cell proteins were solubilized in 0.5 M NaOH at 100° C. for 10 minutes and assayed spectrophotometrically by the method of Lowry et al. (1951, Journal of Biological Chemistry (193), 265-275.). Standards were prepared with bovine plasma γ-globulin in 0.5 M NaOH. Total DNA was extracted from the different fractions (Hendrickx et al., 2006, FEMS Microbiology Ecology 55: 262-273.) and the diversity of the microbial community was evaluated via Denaturating gradient Gel Electrophoresis (DGGE) of 16S rRNA-gen fragments (63-518) amplified using general eubacterial primers. The highest amounts of biomass were found near the entrance of the columns and near the oxygen addition points (150 mm) (FIG. 3). Although the protein concentration in the inoculated column is significantly higher than in the control columns, also in the latter ones increases amounts were detected. This can be explained by microbial contamination in the columns after months of semi-sterile operation. Based on PCR-DGGE DNA fingerprints the inoculated MTBE/TBA-degrading consortium could clearly be visualised in most carrier materials. In the non-inoculated control the consortium was not detected.

Figure 10:
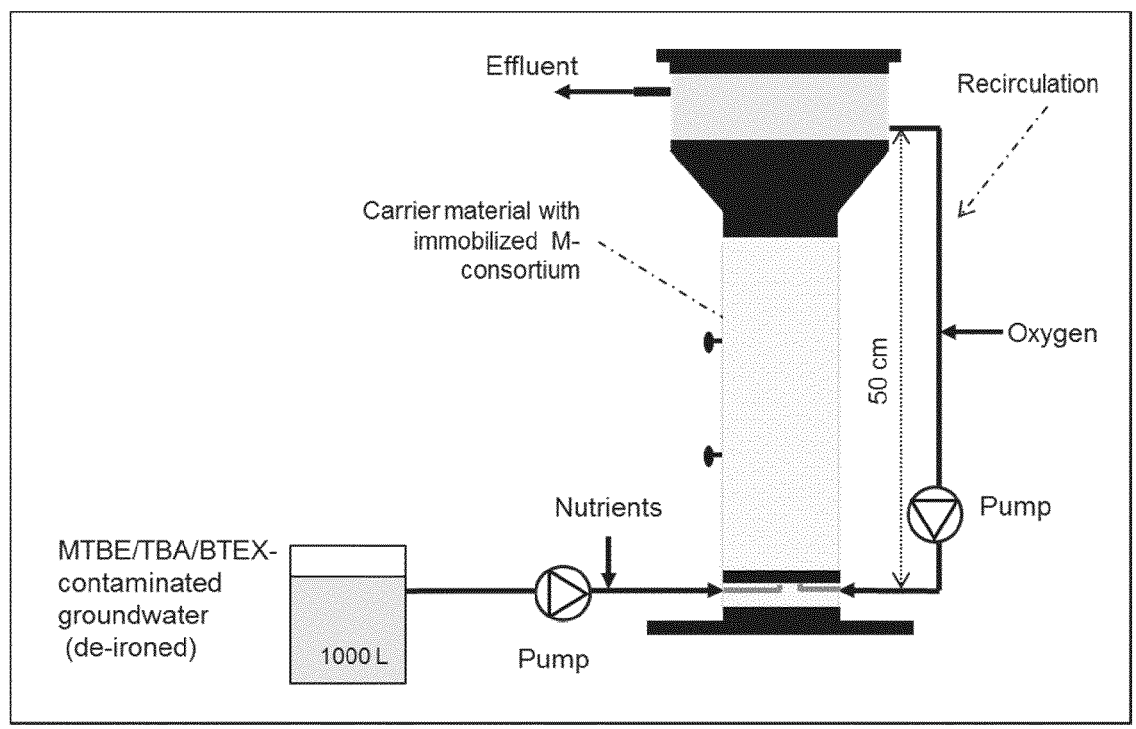
FIG. 10 illustrates a schematic overview of an exemplary reactor set-up according to a particular embodiment envisaged herein showing the pumps, the tubing and the four sampling points.

Example 8: Bioremediation of MTBE-Contaminated Groundwater Using a Fixed Bed Reactor Inoculated with the M-Consortium A schematic picture of the reactor set-up is provided in FIG. 10. This illustrates an exemplary set up but it will be understood that other set-ups can be developed by the skilled person. The reactor consisted of PVC connectors and PVC tubes, with a height of 63 cm and total volume of 7 L, including a recirculation loop. About 1.5 kg of expanded clay particles (ECP, 4 to 5 mm, Argex, Zwijndrecht, Belgium) were used as carrier material for immobilisation of the M-consortium. The pore volume of the reactor was 3.8 L. The reactor was operated as an upflow fixed bed reactor and fed using a peristaltic pump (Watson Marlow, Cornwall, England) from a 1000 L cubitainer containing the influent (FIG. 10). The influent used consisted of roundwater originating from a contaminated gasoline station site and sampled at the effluent of a de-ironing unit. Before use, the pH was adjusted to pH 7.5 and MTBE was added to reach a final concentration 5 mg/L. The groundwater was recirculated from above the carrier material to the reactor base at 10× to 20× the influent flow rate, using a peristaltic pump. Oxygen was added to the groundwater in the recirculation loop using pure oxygen. Just before the influent sampling point and the reactor inlet, a nutrient solution ($K_2HPO_4.3H_2O$ and $KNO_3$, pH 7) was added to the influent using a syringe pump at 200-400 μL/h, to achieve a C/N/P ratio of 100/10/10 in the influent based on weight (2.5 mg/L $K_2HPO_4.3H_2O$ and $KNO_3$). The reactor was equipped with four sampling points, i.e., to sample the influent the effluent and the water inside the reactor at two different heights (FIG. 10 Regularly, the reactor was sampled at the different sampling points using 10 mL glass syringes with a Luer lock tip All samples were analysed for MTBE, TBA and BTEX concentrations and for temperature, pH and dissolved oxygen concentration (see above).

The reactor was operated for 130 days. The MTBE concentrations in the influent, in the reactor and in the effluent in function of the implemented HRT are summarized in FIG. 11. The pH of the influent of the reactor was between 6.9 and 8.0 and was lowered to a pH between 6.8 and 7.4 in the effluent due to biological activity (data not shown). The influent contained DO concentrations between 7 and 23 mg/L due to different oxidation methods in the iron removal system. DO concentrations in the effluent were between 2 and 19 mg/L (FIG. 11(b)). The temperature of the groundwater in the reactor was between 17 and 22° C. (data not shown). The MTBE removal rate was calculated as the amount of MTBE removed (mg/L) divided by the hydraulic retention time (h), and is provided in FIG. 11 (a). At day 1, $1.4 \times 10^6$ cfu of the M-consortium/g ECP were added to the reactor. First, the reactor was operated for 14 days under batch conditions to allow attachment of the added cells to the carrier material. Immediately after the inoculation of the reactor, MTBE removal was measured in the reactor. At day 7, when the MTBE concentration in the reactor was below the detection limit of 2 μg/L, 5 mg/L MTBE and nutrients were added to the reactor. Upon implementing a continuous operation mode with an HRT of 6.4 h at day 14, removal of MTBE was recorded at day 17 with an effluent concentration of MTBE of about 2 mg/L, corresponding to a MTBE removal percentage of 77% due to nutrient limitation. The TBA concentration in the effluent was below the detection limit of 65 μg/L (data not shown). No changes in the removal efficiency were observed during 25 days. At day 42, a continuous dosing of nutrient was installed, upon which the MTBE removal percentage increased from 77% to >99% from day 49 onwards (FIG. 11 (a)). As such, MTBE effluent concentrations of 0.01-0.03 mg/L were obtained at an HRT of 6.4 h, with TBA concentrations in the effluent ranging from below the detection limit of 0.065 to 0.08 mg/L (data not shown). Steady state conditions at all HRTs were allowed for at least 3 days, i.e., a minimum of 12 pore volumes at an implemented HRT of 6 h. Starting at day 53, the implemented HRT was gradually decreased from 6.4 h to 0.7 h in a time span of 59 days by increasing the influent and the nutrient flow rate. For this period, MTBE influent concentrations, which varied between 2 and 5 mg/L, were removed to concentrations below the discharge limit of 0.1 mg/L MTBE in the effluent at HRTs of 6.4 to 1.6 h. The maximal MTBE and TBA effluent concentrations during these adaptation phases were 0.4 mg/L and 0.1 mg/L, respectively. At an implemented HRT of 1.6 h, only a 3 day response time was needed until full removal of MTBE was recovered (effluent concentration of 0.043 mg/L MTBE). Under those conditions, MTBE effluent concentrations as low as 1 μg/L and MTBE removal percentages of above 99.98% were recorded. At an HRT of 0.6 h, the effluent MTBE concentrations increased to between 2.3 and 3.8 mg/L. However, TBA effluent concentrations were still below the detection limit during this period, with one peak of 0.14 mg/L TBA. Therefore, the minimal HRT implying total MTBE removal to below the discharge limit for MTBE was 1.6 h. The highest recorded MTBE removal rate implying complete MTBE removal was 2.5 mg MTBE/L h, measured at day 104 at an implemented HRT of 1.6 h (FIG. 11b). The bioreactor recovered rapidly after sudden increase in MTBE concentration and removal of MTBE was proven to be purely biological.

Example 9: Treatment of MTBE/TBA Contaminated Groundwater in a Pilot Bioreactor System Inoculated with the M-Consortium The performance at pilot scale of a bioreactor inoculated with the M-consortium was evaluated using a 300 L prototype bioreactor which was an upscaling of the system presented in FIG. 10. It concerns an upflow bioreactor where MTBE/TBA-containing water was pumped from bottom to top through a bed of carrier materials inoculated with the M-consortium. The bioreactor was operated as a partially floating bed system with predominantly polystyrol granulates (PSG, Sarstedt, Nümbrecht, Germany). A water recirculation loop returned part of the water from the top to the bottom of the reactor to (1) improve the homogeneity of the bioreactor and (2) to supply oxygen to the bioreactor. The outlet for the treated water is situated at the top of the reactor. Besides addition of oxygen, a continuous nutrient (Nitrogen & phosphor) dosing system and pH-correction system were integrated to create more optimal condition for the bacterial activity. The bioreactor was integrated in a mobile treatment system consisting of (1) a de-ironing unit, (2) the bioreactor connected to an influent and effluent tank, and (3) a polishing activated carbon filter.

The M-consortium was cultivated in the lab on medium WXP (see example 1) using MTBE as sole carbon source. The bioreactor system was uploaded off-site with 4 L of the M-consortium (>8.2 $10^8$ cells/ml, assuming one 16S RNA-gene copy per cell). The reactivity of the system was demonstrated during a 1 month of recirculation mode operation, and subsequently a 1 month of continuous operation (Hydraulic retention time=10 h) with groundwater artificially polluted with 8 mg/L MTBE and 4 mg/L TBA. An efficient removal (>97%) was observed (results not shown).

Figure 12:
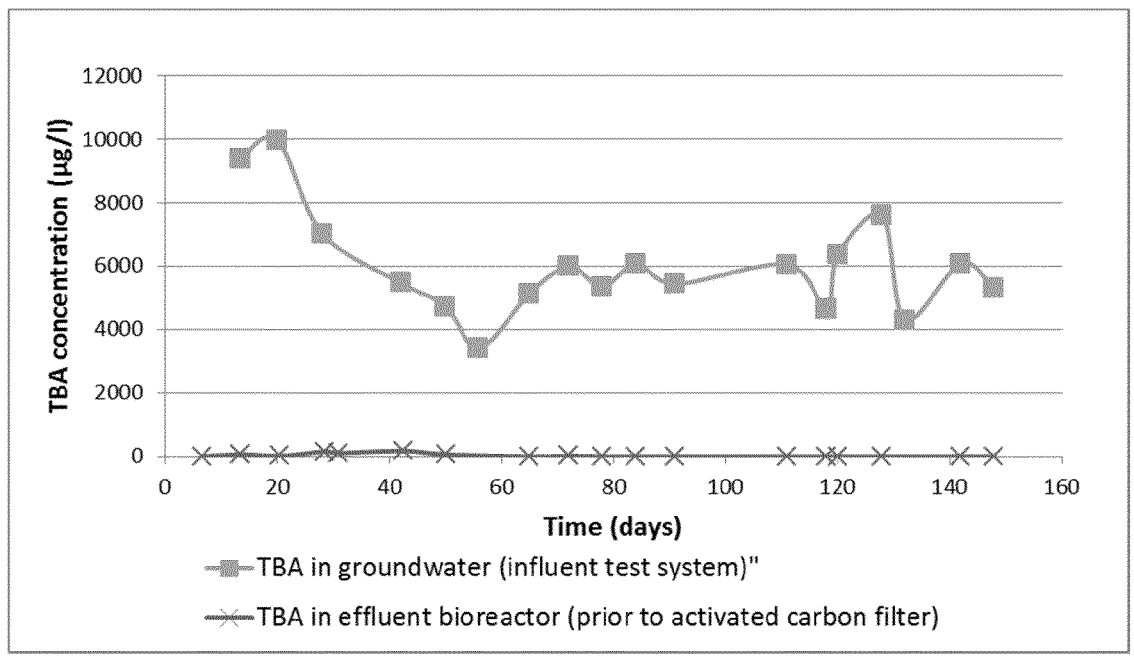
FIG. 12 illustrates the evolution over time (days) of the TBA-concentration (μg/L) in the influent and effluent of a pilot scale bioreactor (300 L) inoculated with the M-consortium.

Next, the pilot scale inoculated bioreactor (300 L) was transported to a real contaminated site to evaluate its performance under real site conditions during a 5 month test period. The test site was an industrial site (chemical storage) where the pumped groundwater used as influent for the pilot system contained MTBE 300-5000 µg/L MTBE as well as 3500-10000 µg/L TBA. FIG. 12 shows the evaluation of the TBA concentration over time in the influent of the pilot system and the effluent of the bioreactor (prior to the GAC step). Both MTBE and TBA were found to be removed efficiently (below 100 µg/L) by the pilot system, which was operated at low flows (50 L/h, HRT=6 h) (table 2). The MTBE concentrations were reduced from concentrations up to 4.500 µg/L till concentration below 110 µg/L (>97% removal). TBA concentrations up to 10.000 µg/L were reduced below 180 µg/L (>98% removal). The activated carbon filter, included in the system as polishing step, reduced the effluent concentration further below 100 µg/L, mostly below detection limit. The high concentrations of dissolved iron in the groundwater were the reason why higher flows (100 l/h, HRT=3 h) were only implemented for a short time. Although a number of non-ideal but realistic situations were applied to the system (fluctuations of pH, temperature increases above 30° C., non-operational periods, fluctuation of flow, . . . ), the system adapted fast and remained active without a need for re-inoculation.

TABLE 2

Operational data for pilot bioreactor test with M-consortium

| Parameter | Parameter specification for pilot test |
|---|---|
| Test location | Industrial site (chemical storage) where groundwater contained TBA (5-75 mg/L) and MTBE (1-12 mg/L) |
| Carrier material in bioreactor | PSG + sponges |
| Total Fe in groundwater | 50 mg/L |
| Hydraulic retention time in bioreactor (h) | 6 h |
| MTBE-influent (µg/L) | 300-5000 µg/L |
| MTBE removal % | >97% |
| TBA-influent (µg/L) | 3500-10000 µg/L |
| TBA removal (%) | >98% |
| Duration test (months) | 5 months |

Based on the 16S rRNA gene sequences displayed in FIGS. 3 to 5, specific qPCR primers and FISH primers were developed and used to determine the abundance of *Methylibium* sp. LD3, *Hydrogenophaga* sp. LD1 and *Mycobacterium* sp. LD6 in pilot treatment system. Based on FISH, these three isolates from the M-consortium represented 25% of the total bacteria in the effluent of the bioreactor. In sludge from the bioreactor and on the carrier material, this was on average 20% (5 data points) and 26% (3 data points), respectively. In the de-ironing unit, up to 31% of the total bacteria could be linked to key-organisms in the M-consortium. Based q-PCR analyses, the sums of *Methylibium* sp. LD3, *Hydrogenophaga* sp. LD1 and *Mycobacterium* sp. LD6 were quantified to be on average 1.4 $10^4$ cells/ml in the effluent of the bioreactor (6 data points), 9 $10^6$ cells/g in the sludge from the bioreactor (4 data points), 3.5 $10^7$ cells/g on the carrier materials (2 data points). In the bioreactor, the *Methylibium* strain remained dominant during the whole test period, but also the *Hydrogenophaga* and the *Mycobacterium* species was found present at different sampling times (table 3).

TABLE 3

Absolute abundance of *Methylibium* sp. LD3, *Hydrogenophaga* sp. LD1 and *Mycobacterium* sp. LD6 in the pilot bioreactor system inoculated with the M-consortium, as determined by q-PCR.

| Sludge samples from bioreactor | *Methylibium* sp. LD3 (copies/g) | *Hydrogenophaga* sp. LD1 (copies/g) | *Mycobacterium* sp LD 6 (copies/g) |
|---|---|---|---|
| Sample 1 | 2.39 $10^7$ | <$10^4$ | <$10^4$ |
| Sample 2 | 1.73 $10^7$ | 1.29 $10^7$ | 4.25 $10^5$ |
| Sample 3 | 2.74 $10^5$ | 3.81 $10^5$ | <$10^4$ |
| Sample 4 | 3.41 $10^6$ | 8.90 $10^5$ | 5.05 $10^4$ |
| Sample 5 | 6.73 $10^5$ | 3.45 $10^5$ | <$10^4$ |

The invention claimed is:

1. A method for degrading one or more of methyl-tertiary-butyl-ether (MTBE), tert-butanol (TBA), formaldehyde (HCHO), and combinations thereof in a contaminated medium, the method comprising the steps of:
   (i) providing an isolated *Methylibium* strain LD3, consisting of the *Methylibium* strain LD3 deposited as LMG P-27480; and
   (ii) treating the contaminated medium with bacteria consisting essentially of said isolated *Methylibium* strain LD3 to degrade at least a portion of said contaminated medium to an MTBE concentration of less than 300 μg/L, a TBA concentration of less than 700 μg/l, and a HCHO concentration below 200 μg/L.

2. The method according to claim 1, wherein the treatment takes place in a bioreactor or in situ by addition of the isolated *Methylibium* strain LD3 to the contaminated medium.

3. The method according to claim 1, wherein the isolated *Methylibium* strain LD3 is added at a cell count of $10^4$ to $10^8$ copies per ml.

4. The method according to claim 1, further comprising determining the concentration of one or more of the MTBE, TBA, HCHO, and combinations thereof in the medium.

5. The method according to claim 1, wherein the contaminated medium comprises one or more of contaminated soil, contaminated sludge, contaminated sediment, contaminated dredge tailing, contaminated chemical waste, contaminated fluid, contaminated water, and combinations thereof.

6. The method according to claim 1, further comprising determining the degradation rate of one or more of the MTBE, TBA and HCHO in the medium.

* * * * *

SEQUENCE LISTING

<160> NUMBER OF SEQ ID NOS: 3

<210> SEQ ID NO 1
<211> LENGTH: 1661

```
<212> TYPE: DNA
<213> ORGANISM: Methylibium sp.

<400> SEQUENCE: 1
tgaattgtaa tacgactcac tatagggcga attgggccct ctagatgcat gctcgagcgg     60
ccgccagtgt gatggatatc tgcagaattc gcccttagag tttgatcctg gctcagattg    120
aacgctggcg gcatgcctta cacatgcaag tcgaacggca gcacgggagc aatcctggtg    180
gcgagtggcg aacgggtgag taatacatcg gaacgtgccc agttgtgggg gatagcccgg    240
cgaaagccgg attaataccg catacgacct acgggtgaaa gcggggatc gcaagacctc     300 gcgctattgg agcggccgat gtcggattag ctagttggtg gggtaaaagc ctaccaaggc    360
tacgatccgt agctggtctg agaggacgac cagccacact gggactgaga cacggcccag    420
actcctacgg gaggcagcag tggggaattt tggacaatgg gcgcaagcct gatccagcca    480
tgccgcgtgc gggaagaagg ccttcgggtt gtaaaccgct tttgtcaggg aagaaacggt    540
ttgggctaat accccgaact aatgacggta cctgaagaat aagcaccggc taactacgtg    600
ccagcagccg cggtaatacg tagggtgcaa gcgttaatcg gaattactgg gcgtaaagcg    660
tgcgcaggcg gctttgcaag acagatgtga atccccggg ctcaacctgg gaactgcatt     720
tgtgactgca aggctggagt gcggcagagg gggatggaat tccgcgtgta gcagtgaaat    780
gcgtagatat gcggaggaac accgatgcg aaggcaatcc cctgggcctg cactgacgct     840
catgcacgaa agcgtgggga gcaaacagga ttagataccc tggtagtcca cgccctaaac    900
gatgtcaact ggttgttgga cggcttgctg ttcagtaacg aagctaacgc gtgaagttga    960
ccgcctgggg agtacggccg caaggttgaa actcaaagga attgacgggg acccgcacaa   1020
gcggtggatg atgtggttta attcgatgca acgcgaaaaa ccttacctac ccttgacatg   1080
tctagaagtt accagagatg gtttcgtgct cgaaagagaa ctagaacaca ggtgctgcat   1140
ggccgtcgtc agctcgtgtc gtgagatgtt gggttaagtc cgcaacgag cgcaacccctt   1200 gtcattagtt gctacgtaag ggcactctaa tgagactgcc ggtgacaaac cggaggaagg   1260
tggggatgac gtcaggtcat catggcccct atgggtaggg ctacacacgt catacaatgg   1320
ccggtacaga gggctgccaa cccgcgaggg ggagccaatc ccagaaaacc ggtcgtagtc   1380
cggatcgcag tctgcaactc gactgcgtga agtcggaatc gctagtaatc gcggatcagc   1440
ttgccgcggt gaatacgttc ctgggtcttg tacacaccgc ccgtcacacc atgggagcgg   1500
gttctgccag aagtagttag cctaaccgca aggagggcga ttaccacggc agggttcgtg   1560
actggggtga agtcgtaaca aggtaaccaa gggcgaattc cagcacactg gcggccgtta   1620
ctagtggatc cgagctcggt accaagcttg gcgtaatcat g                       1661

<210> SEQ ID NO 2
<211> LENGTH: 1665
<212> TYPE: DNA
<213> ORGANISM: Hydrogenophaga sp.

<400> SEQUENCE: 2
catgattacg ccaagcttgg taccgagctc ggatccacta gtaacggccg ccagtgtgct     60
ggaattcgcc cttagagttt gatcctggct cagattgaac gctggcggca tgctttacac    120
atgcaagtcg aacggtaaca ggccgcaagg tgctgacgag tggcgaacgg gtgagtaatg    180
catcggaacg tgcccagtcg tgggggataa cgcagcgaaa gctgtgctaa taccgcatac    240
gatctatgga tgaaagcggg ggaccgtaag gcctcgcgcg attggagcgg ccgatgtcag    300
```

-continued

```
attagctagt tggtggggta aaggcccacc aaggcgacga tctgtagctg gtctgagagg    360
acgaccagcc acactgggac tgagacacgg cccagactcc tacgggaggc agcagtgggg    420
aattttggac aatgggcgca agcctgatcc agcaatgccg cgtgcaggaa gaaggccttc    480
gggttgtaaa ctgcttttgt acggaacgaa acggtctggg ttaataccct gggctaatga    540
cggtaccgta agaataagca ccggctaact acgtgccagc agccgcggta atacgtaggg    600
tgcaagcgtt aatcggaatt actgggcgta aagcgtgcgc aggcggtgat gtaagacagt    660
cgtgaaatcc ccgggctcaa cctgggaatt gcgattgtga ctgcatcgct ggagtgcggc    720
agaggggat ggaattccgc gtgtagcagt gaaatgcgta gatatgcgga ggaacaccga    780
tggcgaaggc aatcccctgg gcctgcactg acgctcatgc acgaaagcgt ggggagcaaa    840
caggattaga taccctggta gtccacgccc taaacgatgt caactggttg ttgggtctct    900
tctgactcag taacgaagct aacgcgtgaa gttgaccgcc tggggagtac ggccgcaagg    960
ttgaaactca aaggaattga cggggacccc acaagcggt ggatgatgtg gtttaattcg   1020
atgcaacgcg aaaaacctta cccacctttg acatgtacgg aatttgccag agatggctta   1080
gtgctcgaaa gagaaccgta acacaggtgc tgcatggctg tcgtcagctc gtgtcgtgag   1140
atgttgggtt aagtcccgca acgagcgcaa cccttgtcat tagttgctac attcagttgg   1200
gcactctaat gagactgccg gtgacaaacc ggaggaaggt ggggatgacg tcaagtcctc   1260
atgcccctta taggtggggc tacacacgtc atacaatggc cggtacaaag ggtcgcaaac   1320
ccgcgagggg gagccaatcc atcaaagccg gtcgtagtcc ggatcgcagt ctgcaactcg   1380
actgcgtgaa gtcggaatcg ctagtaatcg tggatcagca tgtcacggtg aatacgttcc   1440
cgggtcttgt acacaccgcc cgtcacacca tgggagcggg tctcgccaga agtagttagc   1500
ctaaccgcaa ggagggcgat taccacgcg gggttcgtga ctggggtgaa gtcgtaacaa   1560
ggtagccgta agggcgaatt ctgcagatat ccatcacact ggcggccgct cgagcatgca   1620
tctagagggc ccaattcgcc ctatagtgag tcgtattaca attca                   1665
```

<210> SEQ ID NO 3
<211> LENGTH: 1652
<212> TYPE: DNA
<213> ORGANISM: Mycobacterium sp.

<400> SEQUENCE: 3

```
tgaattgtaa tacgactcac tatagggcga attgggccct ctagatgcat gctcgagcgg     60
ccgccagtgt gatggatatc tgcagaattc gcccttagag tttgatcctg gctcaggacg    120
aacgctggcg gcgtgcttaa cacatgcaag tcgaacggaa aggcccttcg ggtgctcga    180
gtggcgaacg ggtgagtaac acgtgggtga tctgccctgc actttgggat aagcctggga    240
aactgggtct aataccgaat aggactccgg actgcatggt ctggggtgga aagcttttgc    300
ggtgtgggat gggcccgcgg cctatcagct tgttggtggg gtgatggcct accaaggcga    360
cgacgggtag ccggcctgag agggtgaccg gccacactgg gactgagata cggcccagac    420
tcctacggga ggcagcagtg gggaatattg cacaatgggc gcaagcctga tgcagcgacg    480
ccgcgtgagg gatgacggcc ttcgggttgt aaacctcttt cagcacagac gaagcgcaag    540
tgacggtatg tgcagaagaa ggaccggcca actacgtgcc agcagccgcg gtaatacgta    600
gggtccgagc gttgtccgga attactgggc gtaaagagct cgtaggtggt ttgtcgcgtt    660
gttcgtgaaa actcacagct taactgtggg cgtgcgggcg atacgggcag actgagtac    720
tgcaggggag actggaattc ctggtgtagc ggtggtatgc gcagatatca ggaggaacac    780
```

```
cggtggcgaa ggcgggtctc tgggcagtaa ctgacgctga ggagcgaaag cgtggggagc        840
gaacaggatt agataccctg gtagtccacg ccgtaaacgg tgggtactag gtgtgggttt        900
ccttccttgg gatccgtgcc gtagctaacg cattaagtac cccgcctggg gagtacggcc       960
gcaaggctaa aactcaaagg aattgacggg ggcccgcaca agcggcggag catgtggatt      1020
aattcgatgc aacgcgaaga accttacctg ggtttgacat gcacaggacg ccggcagaga      1080
tgtcggttcc cttgtggcct gtgtgcaggt ggtgcatggc tgtcgtcagc tcgtgtcgtg      1140
agatgttggg ttaagtcccg caacgagcgc aaccccttgtc tcatgttgcc agcacgttat     1200
ggtggggact cgtgagagac tgccggggtc aactcggagg aaggtgggga tgacgtcaag      1260
tcatcatgcc ccttatgtcc agggcttcac acatgctaca atggccggta caaagggctg      1320
cgatgccgtg aggtggagcg aatcctttca aagccggtct cagttcggat cggggtctgc      1380
aactcgaccc cgtgaagtcg gagtcgctag taatcgcaga tcagcaacgc tgcggtgaat      1440
acgttcccgg gccttgtaca caccgcccgt cacgtcatga aagtcggtaa cacccgaagc      1500
cggtggccta accccttgtg ggagggagcc gtcgaaggtg ggatcggcga ttgggacgaa      1560
gtcgtaacaa ggtagccgta agggcgaatt ccagcacact ggcggccgtt actagtggat      1620
ccgagctcgg taccaagctt ggcgtaatca tg                                    1652
```